(12) United States Patent
Xaus Pei et al.

(10) Patent No.: US 7,468,270 B2
(45) Date of Patent: Dec. 23, 2008

(54) PROBIOTIC STRAINS, A PROCESS FOR THE SELECTION OF THEM, COMPOSITIONS THEREOF, AND THEIR USE

(75) Inventors: Jordi Xaus Pei, Granada (ES); Rocío Martin Jiménez, Granada (ES); Juan Miguel Rodríguez Gómez, Granada (ES); Julio Boza Puerta, Granada (ES); Jesús Jiménez López, Granada (ES)

(73) Assignee: Puleva Biotech, S.A., Granada (ES)

( * ) Notice: Subject to any disclaimer, the term of this patent is extended or adjusted under 35 U.S.C. 154(b) by 249 days.

(21) Appl. No.: 11/024,370

(22) Filed: Dec. 28, 2004

(65) Prior Publication Data

US 2005/0244392 A1 Nov. 3, 2005

Related U.S. Application Data

(63) Continuation of application No. PCT/EP03/06752, filed on Jun. 26, 2003.

(51) Int. Cl.
*C12N 1/02* (2006.01)
*C12N 1/04* (2006.01)
*C12N 1/20* (2006.01)

(52) U.S. Cl. ............... 435/252.9; 435/260; 435/261; 435/853

(58) Field of Classification Search .............. None
See application file for complete search history.

(56) References Cited

U.S. PATENT DOCUMENTS 6,107,033 A * 8/2000 Welling et al. ............. 435/6

FOREIGN PATENT DOCUMENTS

| EP | 0577903 | 1/1994 |
|---|---|---|
| EP | 0768375 | 4/1997 |
| WO | 9700078 | 1/1997 |
| WO | 0053200 | 9/2000 |

OTHER PUBLICATIONS

Ivan A. Cassas, et al., Validation of the Probiotic Concept: *Lactobacillus reuteri* Confers Broad-spectrum Protection against Disease in Humans and Animals, 2000, pp. 247-256, ISSN 0891-060X, Department of Microbiology, North Carolina State University.

* cited by examiner

*Primary Examiner*—David M. Naff
*Assistant Examiner*—Deborah K. Ware
(74) *Attorney, Agent, or Firm*—Katten Muchin Rosenman LLP

(57) ABSTRACT

The present invention relates to a novel process for the selection of new probiotic strains which comprises the following steps: a) selecting for non-pathogenic strains which are capable of surviving in breast milk and/or amniotic fluid, and b) selecting for non-pathogenic strains which are able to be transferred to breast milk and/or amniotic fluid after oral intake in healthy individuals without colonizing other internal organs except mucousas. The invention also provides new *Lactobacillus* strains, which are: CECT5711 (*Lactobacillus coryniformis*), CECT5713 (*Lactobacillus salivarius* subsp. *salivarius*), CECT5714: (*Lactobacillus gasseri*, formerly *L. acidophilus*), CETC5715: (*Lactobacillus gasseri*), and CECT5716: (*Lactobacillus fermentum*); and refers to their use for the prophylaxis or treatment against digestive, infective, neuro-degenerative and immune related diseases such as allergies or inflammatory diseases.

5 Claims, 16 Drawing Sheets

SEQUENCE LISTING

```
<160> NUMBER OF SEQ ID NOS: 2

<210> SEQ ID NO 1
<211> LENGTH: 10
<212> TYPE: DNA
<213> ORGANISM: Lactobacillus

<400> SEQUENCE: 1
acgcaggcac                                                          10

<210> SEQ ID NO 2
<211> LENGTH: 21
<212> TYPE: DNA
<213> ORGANISM: Lactobacillus

<400> SEQUENCE: 2
accytrgaag gyggygatgt b                                             21
```

PROBIOTIC STRAINS, A PROCESS FOR THE SELECTION OF THEM, COMPOSITIONS THEREOF, AND THEIR USE

CROSS-REFERENCE TO RELATED APPLICATION

This application is a continuation of an International Application No. PCT/EP03/06752 which was filed on Jun. 26, 2003, which is herein incorporated by reference.

FIELD OF THE INVENTION

The present invention relates to a novel process for the selection of new probiotic strains, to new probiotic microorganisms of the genus *Lactobacillus* selected according to this method and to compositions comprising these microorganisms; to their use for the prophylaxis or treatment against digestive, infective, neuro-degenerative and immune related diseases such as allergies or inflammatory diseases, and to a novel source to obtain said microorganisms.

BACKGROUND OF THE INVENTION

For many years, lactic acid bacteria have been utilized as fermenting agents for the preservation of food taking benefit of a low pH and the action of fermentation products generated during the fermentative activity thereof to inhibit the growth of spoilage bacteria. With this aim, non-well characterized lactic acid bacteria or "fermentum" have been used to prepare a variety of different foodstuffs such as dry fermented meat products, cheese, and other fermented dairy products from milk.

Recently, lactic acid bacteria have attracted a great deal of attention because some strains have been found to exhibit valuable properties to man and animals upon ingestion. In particular, specific strains of the genus *Lactobacillus* or *Bifidobacterium* have been found to be able to colonize the intestinal mucosa and to assist in the maintenance of the well-being of man and animal, and has been named such as probiotics.

Probiotics are considered to be viable microbial preparations which promote the individual's health by preserving a healthier microflora in the intestine. A microbial preparation may be commonly accepted as a probiotic in case the effectual thereof and their mode of action are known. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach. During the extensive studies leading to new probiotic strains, previous patent applications have described the isolation of variety of different bacterial strains from baby feces (JP04320642, JP05227946). Moreover, the probiotic strains obtained up to now were mainly selected for their capability to adhere to the intestinal mucosa, usually by in vitro experiments. Subsequent selection has not always been performed, and if it has, it used to be mainly based on individual properties of the strain. Finally, and sometimes after the commercialization of the strain, the beneficial effects of the selected strain have been proven in vivo.

In this regard, several patent applications such as eg. EP0768375, WO97/00078, EP0577903 and WO00/53200 disclose specific strains of *Bifidibacterium* and *Lactobacillus* and their beneficial effects on diarrhea, immunomodulation, hypersensitivity reactions or infection by pathogen microorganisms.

Moreover, the beneficial effects of human breast milk on the well-being of infants compared to those fed with milk-based formula has also been extensively reported. In this regard, a reduction in the risk of infection, allergy, asthma and related affections, and an improvement of the intestinal maturation and gut functions has been described. Also, it has been reported that the composition of the gut flora is different to human-milk fed infants from those fed with milk-based formula. The beneficial effects and the modulation of the gut flora of breast human milk have been attributed to its characteristic composition as compared to infant formulas. Thus, the benefits of breast milk proteins such as lactoferrin or maternal immunoglobulins, and the rich composition in oligosaccharides that may act as prebiotic compounds, in the regulation of the flora and gut functions have been reported.

However, to our knowledge there is no publication or work that describes the presence of microbial strains in normal human breast milk. Neither it has been reported that such microbial strains could be beneficial for the breast-fed baby, and therefore acting as probiotics modulating the gut flora of the breast feeding infant. Our work suggests that the well-being effects of the human breast-fed could be also mediated by microbial strains present therein.

It has been suggested in several works that the initial colonization of the neonate is due to cross-contamination with vaginal microflora during labor. However, there are several studies that show similar initial microbial colonization of the neonate independently of the neonate delivery route (cesarean versus natural labor). Moreover, the fact that it is not possible to obtain germ-free animals from conventional pregnant mice nevertheless they have been obtained by cesarean, and that these animals could also be obtained after embryo delivery to sterile recipient mice (Okamoto, M. and Matsumoto, T. 1999. Exp. Anim. 48: 59-62), suggest to us that it has to be other mechanisms than vaginal contamination that also influences the initial colonization of the neonate, and that this mechanism has to begin before labor.

In this regard, to our knowledge, there is no publication or work describing the presence of lactic acid bacterial strains in normal human amniotic fluid. Neither it has been reported that such non-pathogenic microbial strains could be beneficial for the gestating baby, and therefore conditioning, just during the gestation, the initial microbial populations able to colonize the fetal gut.

In understanding the valuable properties that particular strains of lactic acid bacteria may provide, there is a desire in the art for additional lactic acid bacterial strains that are beneficial to the well being of man and/or animal. Consequently, a problem of the prior art was to provide rational methods for the selection of additional new bacterial strains and novel sources for the selection of them, that allow the obtention of bacterial strains which exhibit individually a high number of beneficial properties for man and/or animals. The above problem has been solved by providing novel microorganisms, namely lactic acid bacteria, belonging to the genus *Lactobacillus*. These new strains have been obtained from different sources apart from feces, such as goat cheese and from human breast milk and amniotic fluid, and have been chosen by a method consisting in the ability of these strains to survive in breast milk and/or amniotic fluid, and by their ability to be transferred to breast milk and/or amniotic fluid after oral intake.

This selection method ensures that the bacterial strains obtained have implicitly most of the characteristics attributed to a potential probiotic strain, namely good resistance to digestion process and the ability of gut colonization, but also a more natural human origin, safety aspects, and the ability to colonize and regulate some human niches other than the gut. Finally, the selected strains have also been tested not only for their adhesion capabilities but for having a high degree of beneficial characteristics.

This figure illustrates the survival rate of the selected probiotic strains of this invention in breast milk and amniotic fluid. According to the selection method, the survival of the potential probiotic strains was measured using human breast milk (grey bars) and amniotic fluid (black bars). $10^8$ cfu of any candidate bacterial strain were resuspended in 1 ml of MRS or breast milk or amniotic fluid, and incubated for 1 hour at 37° C. in anerobic conditions. Survival after culture was assessed cultivating serial dilutions in MRS agar plates. The results are represented as the mean±SD of three independent experiments. Those candidate bacteria that survive more than 75% in at least one of human fluids were initially selected.

Figure 2:
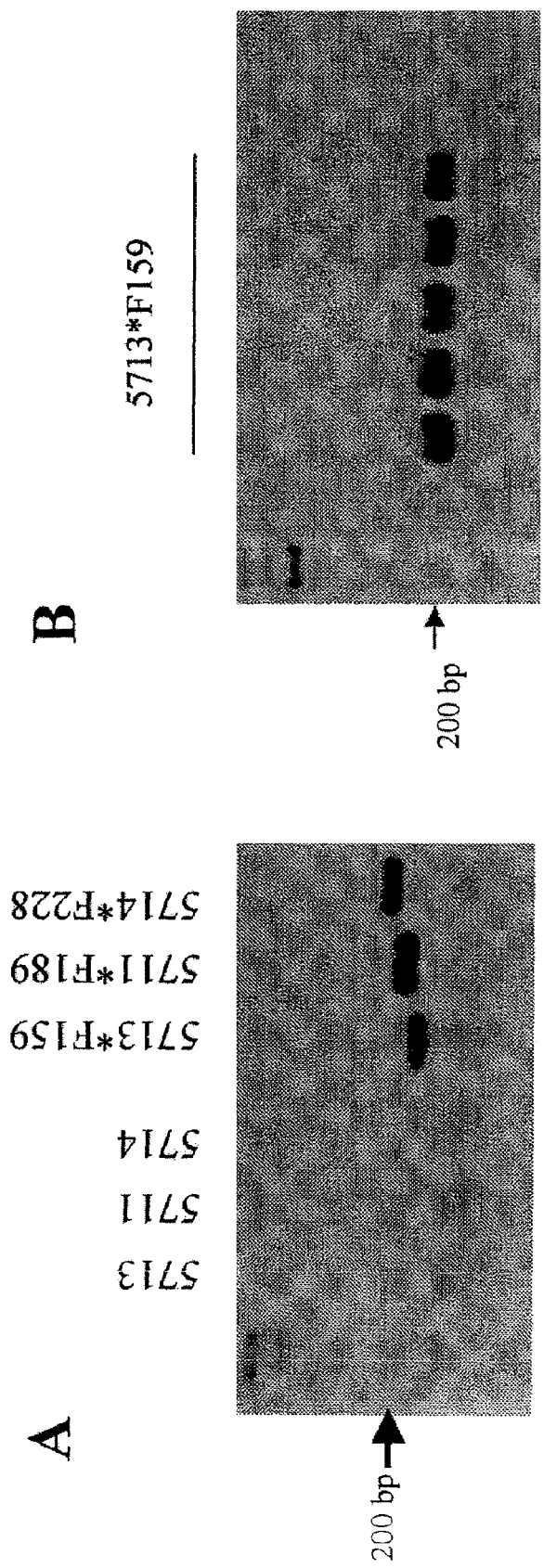

FIG. 2. Screening method: Transfer of bacteria to breast milk.

This figure illustrates the transfer of selected bacteria to breast milk after oral intake. A) Labelling of the strains. Those strains that survive in breast milk and/or amniotic fluid were genetically labeled using a PCR-detectable construction. Different strains are labeled with DNA fragments of different sizes (159 bp:F159; 189 bp: F189; and 228 bp: F228). The PCR signal is only detectable in the genetically labeled strains. The figure shows as example the labeling of the bacterial strains CECT5711, CECT5713 and CECT5714. B) Transfer of selected bacteria to breast milk. The capability of the labeled strains to be transferred to breast milk and/or amniotic fluid was evaluated using pregnant mice as an animal model. Pregnant mice were inoculated every two days with $10^8$ cfu/mice (in this figure we showed results of *L. salivarius* CECT5713) for two weeks before labor. Presence of bacteria in the milk was detected indirectly comparing the number of bacteria PCR-detectable in the gut of neonates before and just after lactating for the first time. Lane 1 in each panel corresponds to the molecular weight marker.

Figure 3:
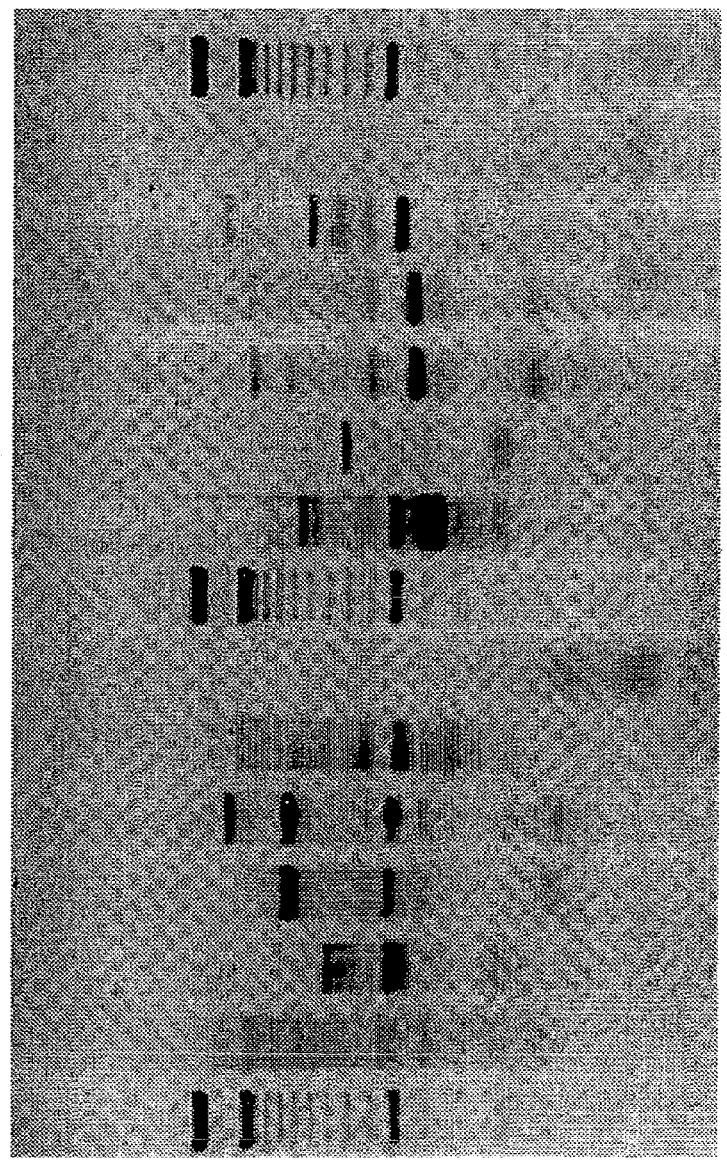

FIG. 3. RAPD profile of the selected bacteria.

This figure illustrates the RAPD profiles of the 5 selected probiotic strains of this invention using two different primers (Argdei and OPL5). Lanes 1, 8 and 15 correspond to the molecular weight marker, lanes 7 and 14 are the negative controls.

Figure 4:
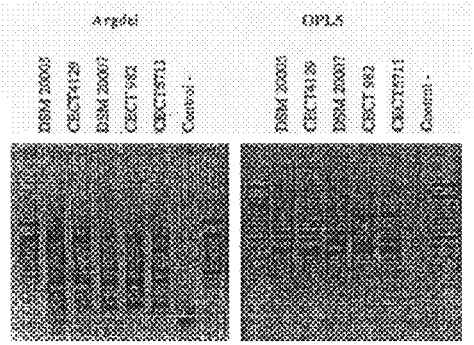
Figure 4:
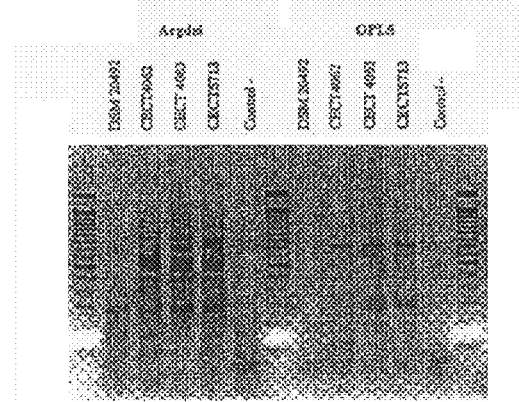
Figure 4:
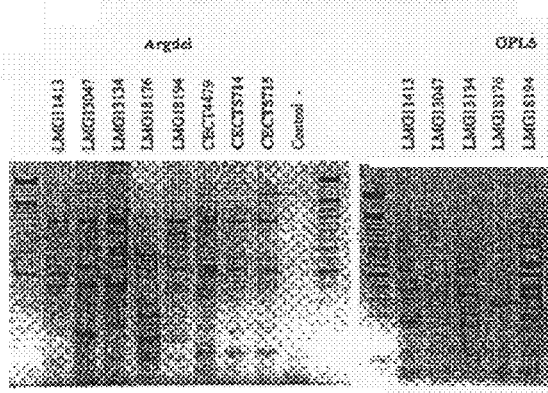
Figure 4:
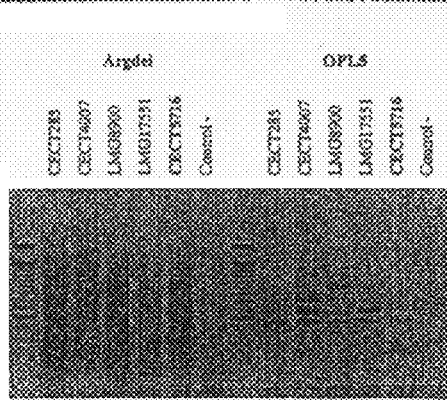

FIG. 4. Comparison of the RAPD profile of the selected bacteria with other bacteria of the same species.

This figure illustrates the differences in RAPD profiles observed between the selected probiotic strains of this invention and those obtained with other bacterial strains of the same species. Each specie is represented in one of the panels: *L. coryniformis* (A), *L. salivarius* (B), *L. gasseri* (C) and *L. fermentum* (D). The strains used are described in Table III.

Figure 5:
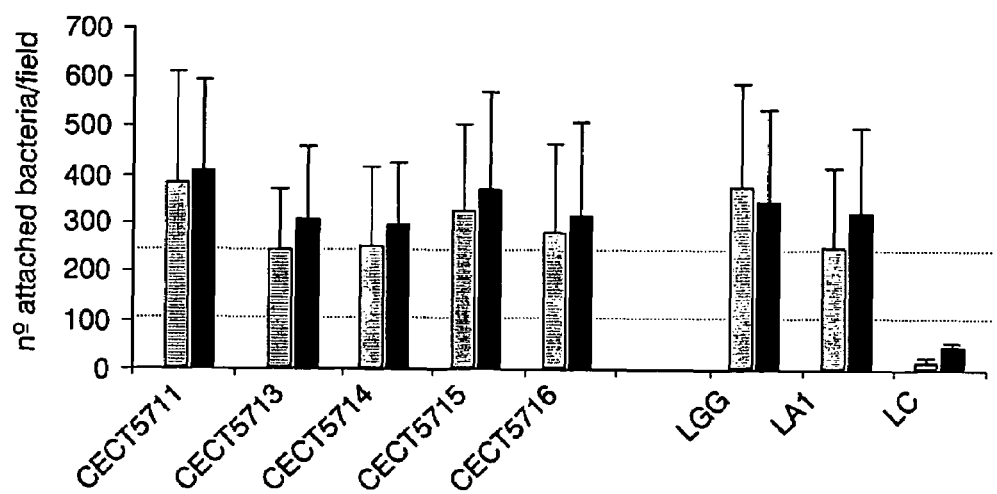

FIG. 5. Adhesion of probiotic strains to intestinal cells.

This figure illustrate the adhesion of probiotic strains to intestinal cells. The adhesion of the probiotic strains of this invention were assessed using Caco-2 (grey bars) or HT-29 (black bars) intestinal cell lines and compared to commercial probiotic strains. Twenty randomized fields were counted and the results expressed as the mean of the number of bacteria attached to the cells per field±SD. The adhesion capability of a probiotic strain to each intestinal cell line was considered high if the number of attached bacteria was >250, moderate between 100 and 250, and slight >100.

Figure 6:
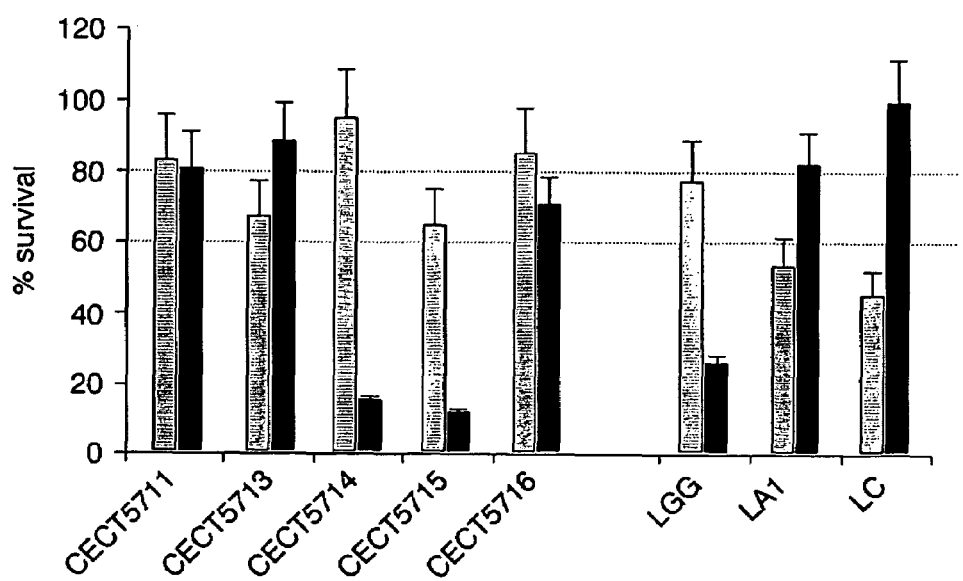

FIG. 6. Survival of probiotics strains to digestion condition.

This figure illustrates the survival of probiotic strains to digestion conditions. The resistance of the probiotic strains of this invention to acidic (grey bars) and high bile salt content (black bars) was assessed in vitro by culture of bacteria in MRS pH 3.0 or 0.15% bile salts for 90 minutes. The results are represented as the mean±SD of three independent experiments. The resistance of a probiotic strain was considered high if the survival was >80%, moderate between 60% and 80%, and slight >60%.

Figure 7:
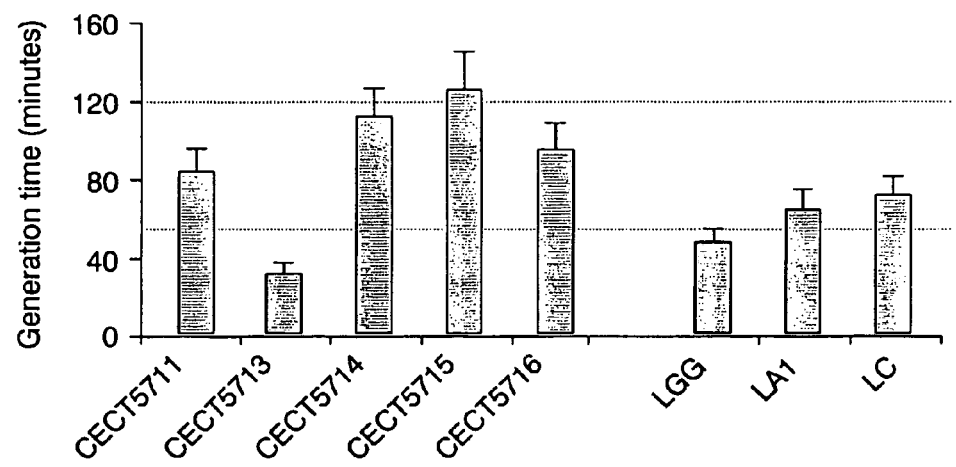

FIG. 7. Generation time of probiotic strains.

This figure illustrates the generation time of probiotic strains. The time of generation of the probiotic strains of this invention was assessed in vitro by cultivating bacteria in MRS 0.2% glucose for 120 minutes. The results are represented in minutes and as the mean ±SD of three independent experiments. The generation time of a probiotic strain was considered rapid if the time was <60, moderate between 60 and 120, and slow >120 minutes.

Figure 8:
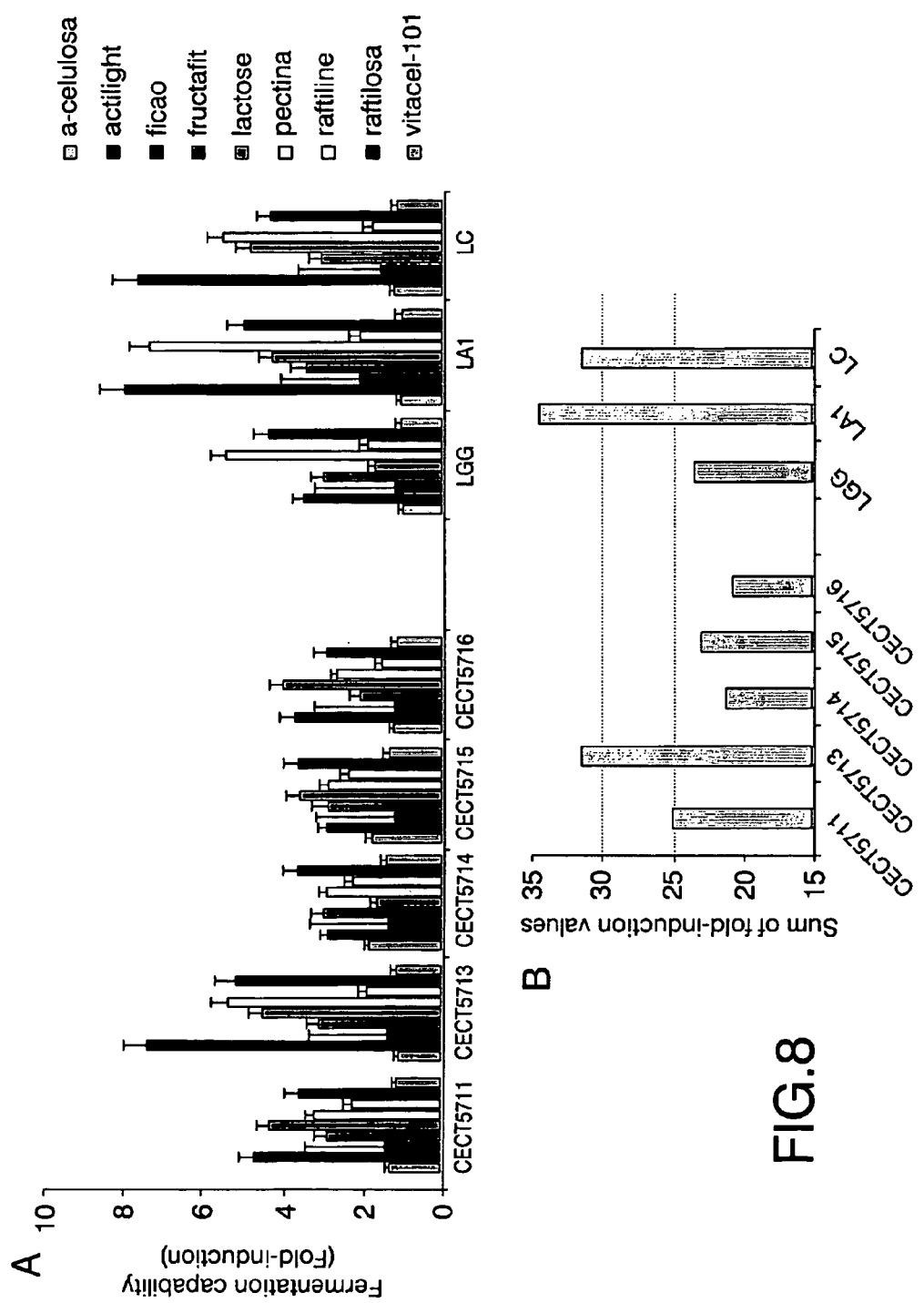

FIG. 8. Fermentation capabilities of probiotic strains

This figure illustrates the ability of probiotic strains to fermentate complex carbohydrates. The fermentation capabilities of the probiotic strains of this invention to use complex carbohydrates as an unique source of carbohydrates was assessed in vitro by cultivating bacteria in MRS without glucose and supplemented with 2% of indicated carbohydrates for 24 and 48 hours. Reduction of the pH was assessed using bromcresol purple. The results are represented as the fold-induction in absorbance after 24 hours compared with a control culture without carbohydrate source (A) and the sum of all independent fold-induction values (B). The fermentation capability of a probiotic strain was considered high if the total value was >30, moderate between 25 and 30, and slight <25.

Figure 9:
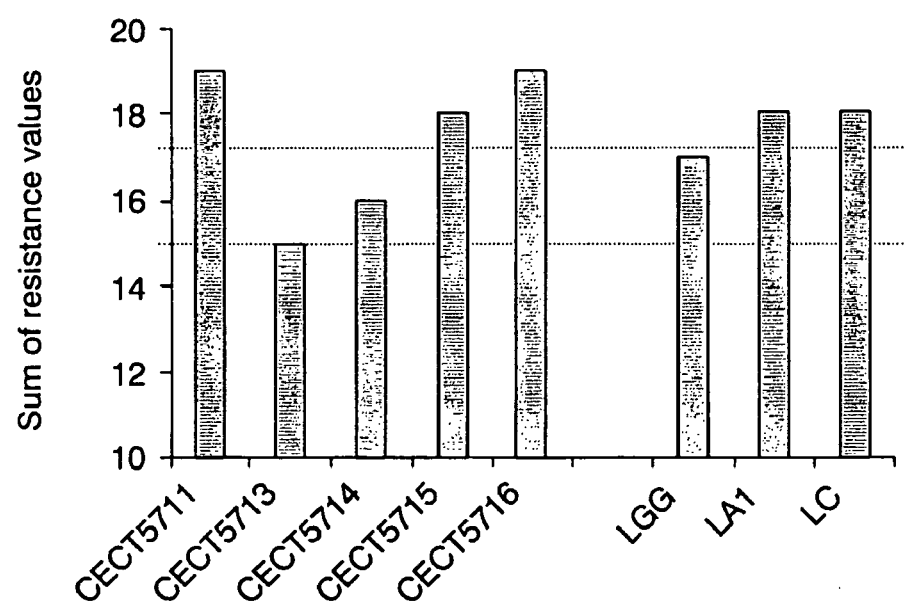

FIG. 9. Resistance to antibiotic of probiotic strains.

This figure illustrates the resistance to antibiotic of probiotic strains. The resistance of antibiotic treatment of the probiotic strains of this invention was assessed in vitro by an agar well diffusion assay in Moeller-Hinton plates for 24-48 hours. The diameter of the hallo of inhibition determines the antibiotic effect. The results are represented as R (resistant) if the hallo has a diameter <12 mm, I (intermediate) from 12 to 15 mm, and S (sensible) if >15 mm. After that, a numerical value was assigned to each condition: R=3, I=2, and S=1. The resistance capability of a probiotic strain was considered high if the total value was >17, moderate between 15 and 17, and slight <15.

Figure 10:
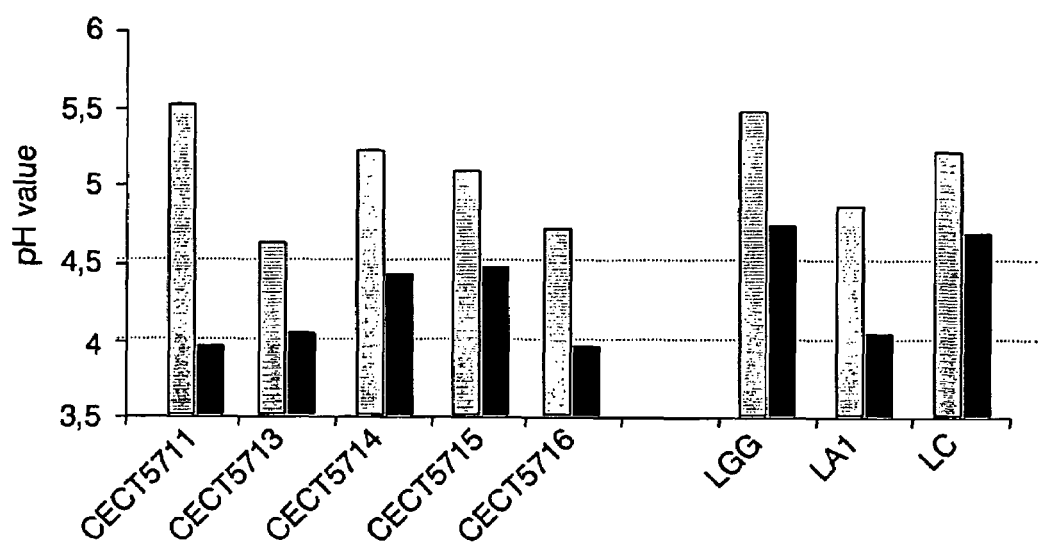

FIG. 10. Acid production by the probiotic strains.

This figure illustrates the acid production by the probiotic strains. The production of acid (lactic, propionic, acetic and butyric acid) by the probiotic strains of this invention was assessed in vitro by the measurement of the pH in milk cultures for 24 (grey bars) and 48 (black bars) hours. The production of acid by a probiotic strain was considered high if the milk pH value after 48 hours was <4, moderate between 4 and 4.5, and slight >4.5.

Figure 11:
Figure 11:
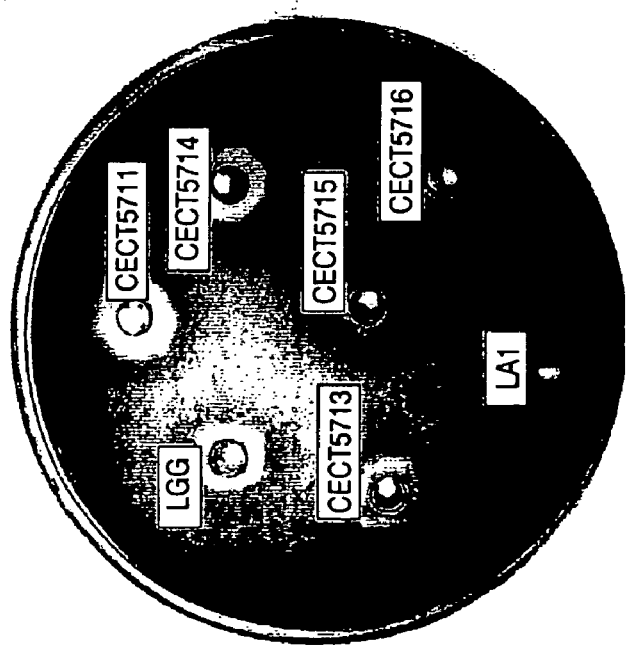

FIG. 11. Production of bactericide metabolites by the probiotic strains.

This figure illustrates the production of antimicrobial metabolites by the probiotic strains. The production of antimicrobial metabolites by the probiotic strains of this invention was assessed in vitro by an agar well diffusion assay in TSA plates cultured with *S. typhimuriumi* (black bars) or *Escherichia coli* (grey bars). The diameter of the hallo (in millimeters) of inhibition induced by the bacterial supernatants determines the bactericide effect. The antimicrobial capability of a probiotic strain was considered high if the hallo was >12, moderate between 8 and 12, and slight <8 for both pathogenic strains.

Figure 12:
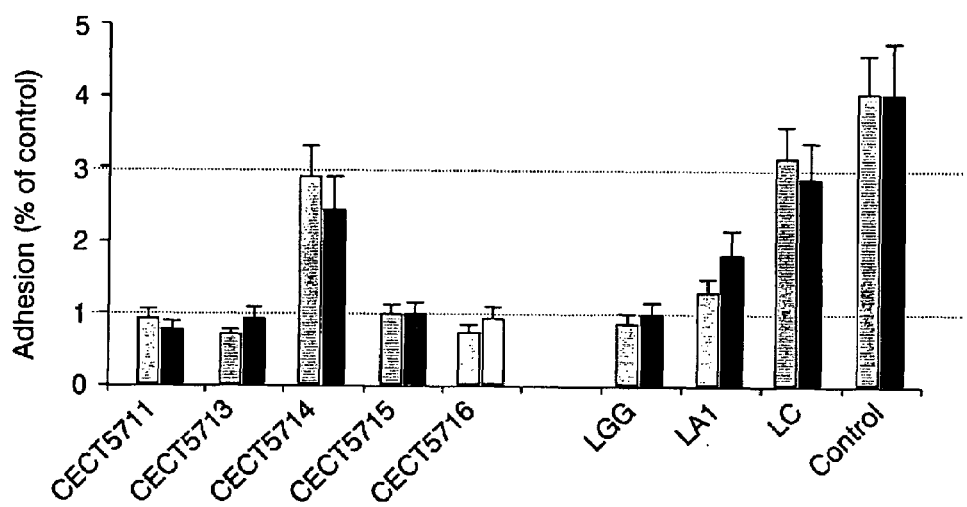

FIG. 12. Inhibition of the adhesion of pathogenic bacteria.

This figure illustrates the inhibition of the adhesion of pathogenic bacteria. The adhesion of the pathogenic strains *E. coli* (grey bars) and *S. typhimurium* (black bars) to Caco-2 cells was assessed in the presence of the probiotic strains of this invention and compared to commercial probiotic strains. Ten randomized fields were counted and the results expressed as the mean of the % of adhered gram-negative bacteria attached to the cells compared to the number of pathogenic bacteria adhered in absence of probiotics. The capability of a probiotic strain to inhibit pathogenic bacteria adherence was considered high if the % of both attached pathogenic bacteria was <25, moderate between 25 and 75, and slight >75.

Figure 13:
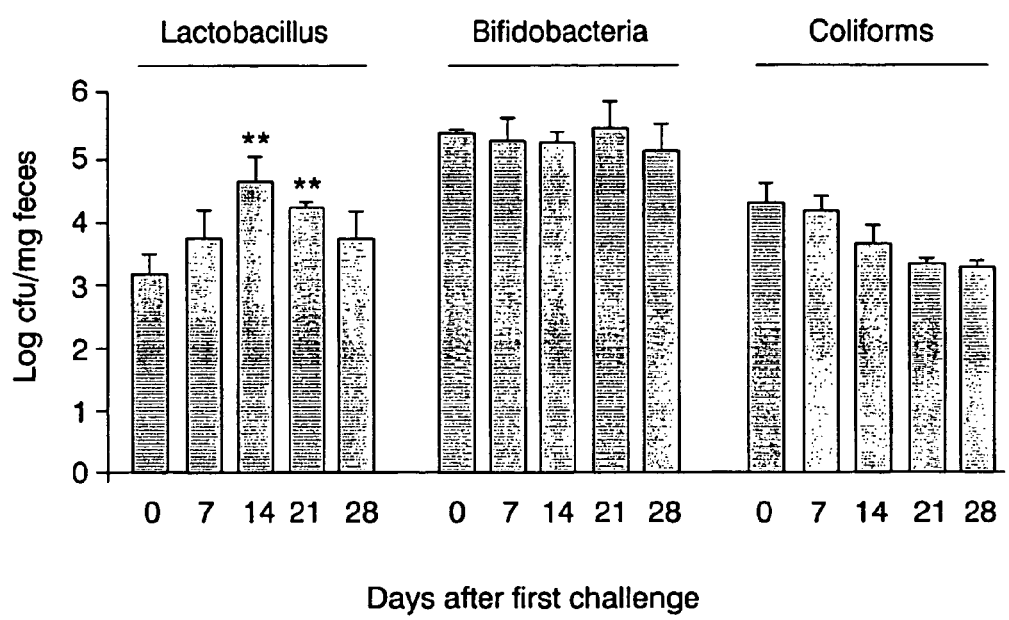

FIG. 13. Gut colonization by *L. Salivarius* CECT5713.

This figure illustrates the gut colonization by *L. salivarius* CECT5713. The number of fecal *lactobacillus, bifidobacteria* and coliform bacteria in mice supplemented daily for 14 days with $10^8$ cfu of *L. salivarius* CECT5713 was analyzed by bacterial platting. Fecal samples (200 mg aprox) were collected at day 0, 7 and 14 of probiotic supplementation and also one and two weeks (day 21 and 28) after supplementation was terminated. (* $p<0.05$; ** $p<0.01$).

Figure 14:
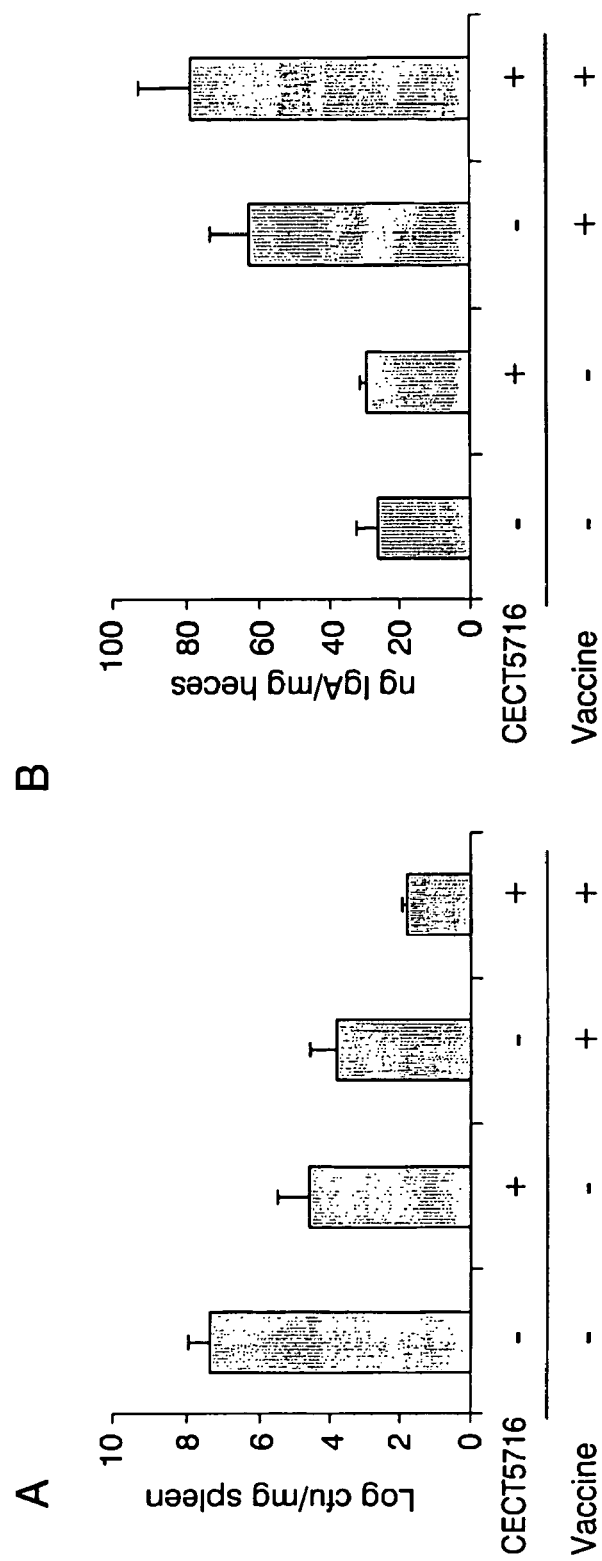

FIG. 14. Effect of *L. Fermentum* CECT5716 on *Salmonella* infection.

This figure illustrates the effect of *L. fermentum* CECT5716 on *Salmonella* infection. A) *L. fermentum* CECT5716 inhibits *Salmonella* translocation to the spleen. The number of *Salmonella* colonies was measured in the spleens of mice treated with *L. fermentum* CECT5716 with or without vaccination with 108 inactivated cfu of *Salmonella* after 24 hour of an oral challenge with $10^{10}$ cfu *Salmonella*. B) The same mice were used to measure the IgA content in feces.

Figure 15:
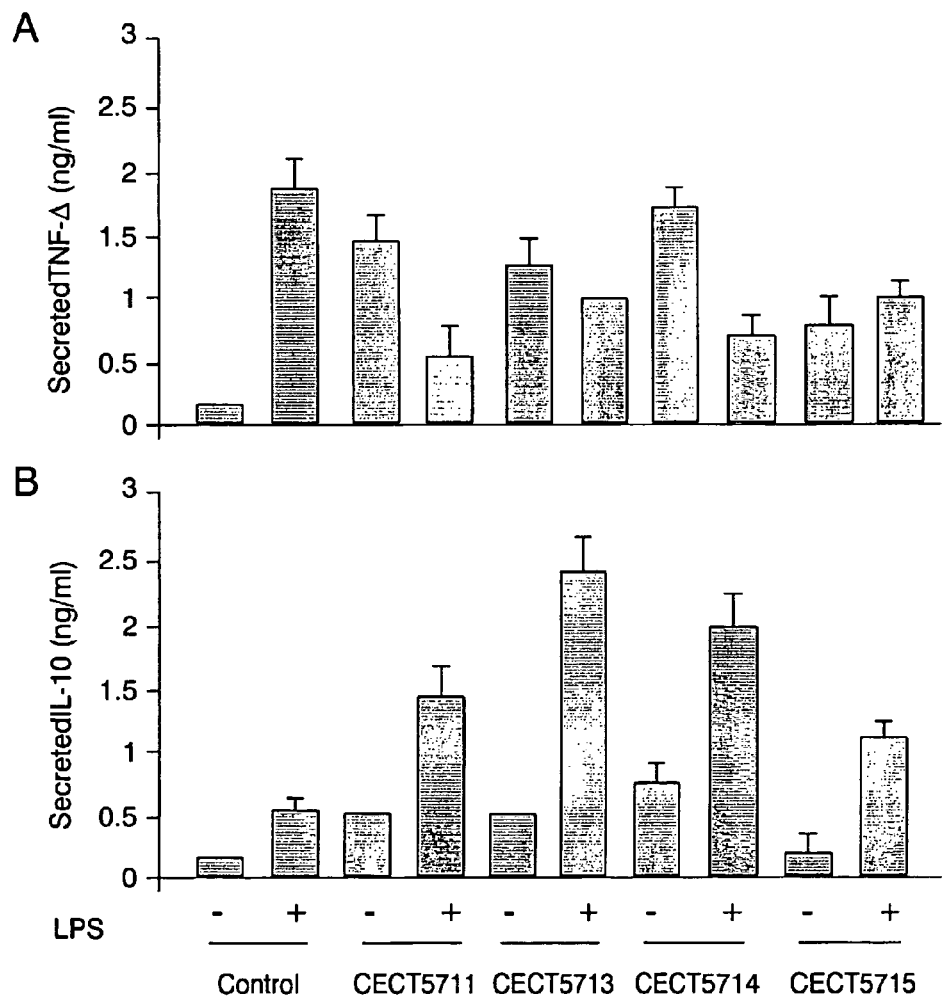

FIG. 15. Effect of probiotic strains on cytokine expression.

This figure illustrates the effect of probiotic strains on cytokine expression. The TNF-α (A) ot IL-10 (B) cytokine production was analyzed in bone marrow derived macrophages stimulated with LPS and the indicated probiotic strain for 12 hours. Cytokine production was detected by an ELISA technique.

Figure 16:
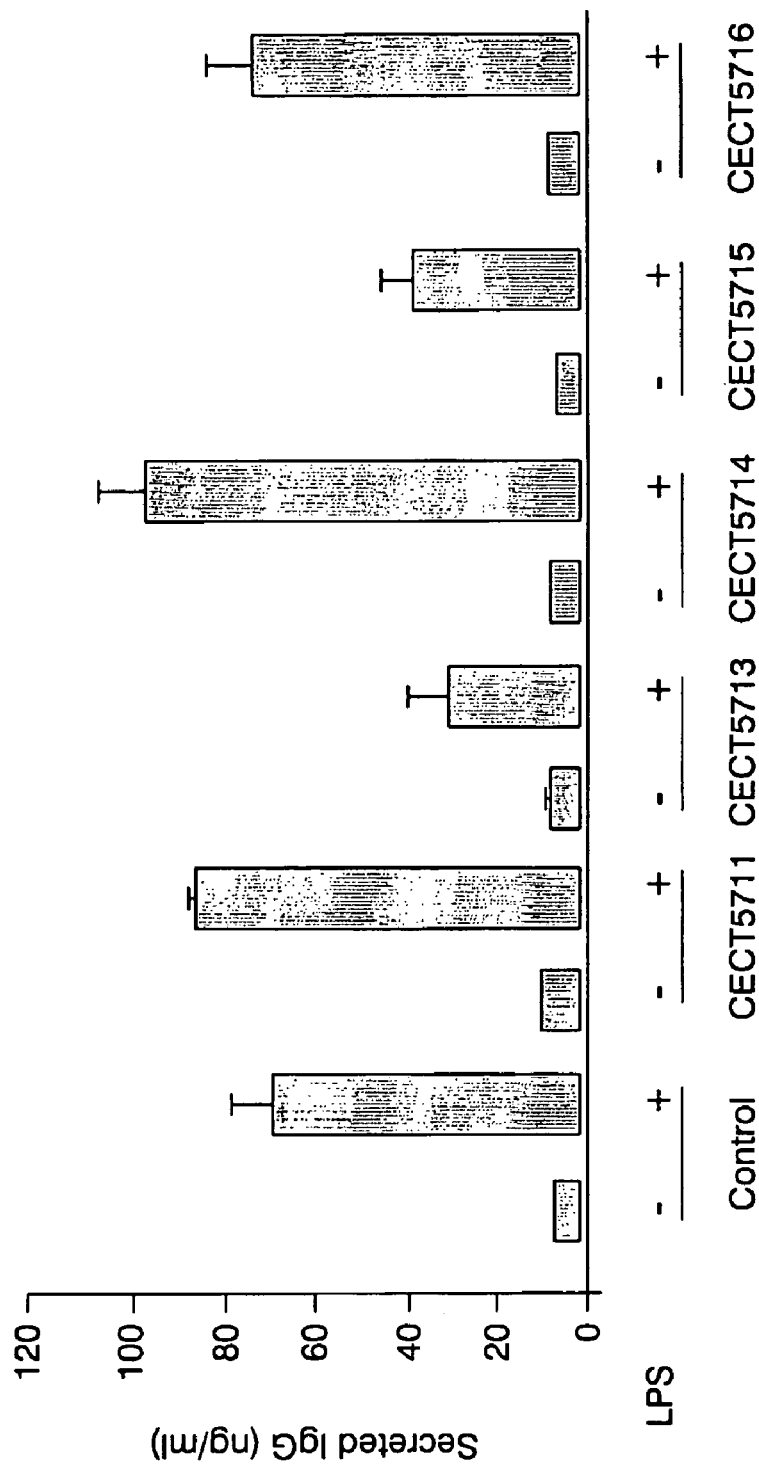

FIG. 16. Effect of probiotic strains on Ig G expression.

This figure illustrates the effect of probiotic strains on Ig G expression. The IgG production was analyzed in lymphocytes obtained from the spleen of Balb/c mice (6-8 weeks old) stimulated with LPS and the indicated probiotic strain for 6 days.

Immunoglobulin production was detected by an ELISA technique from Bethyl.

SUMMARY OF THE INVENTION

The present invention provides, therefore, a method for the selection of probiotic microbial strains, comprising the following steps:
 a. selecting for non-pathogenic strains which are capable of surviving in breast milk and/or amniotic fluid, and
 b. selecting for non-pathogenic strains which are able to be transferred to breast milk and/or amniotic fluid after oral intake in healthy individuals without colonizing other internal organs except mucousas.

In a further aspect, the invention provides new *Lactobacillus* strains, which are:

CECT5711 (*Lactobacillus coryniform*),
CECT5713 (*Lactobacillus salivarius* subsp. *salivarius*),
CECT5714: (*Lactobacillus gasseri*, formerly *L. acidophilus*),
CETC5715: (*Lactobacillus gasseri*), and
CECT5716: (*Lactobacillus fermentum*).

A further aspect of the invention relates to the use of mammal milk and mammal amniotic fluid as a source to obtain non-pathogenic probiotic bacteria.

Another aspect of the invention relates to compositions and products contaning at least one of the strains mentioned above.

Finally, a last aspect of the invention relates to the use of the strains mentioned above or of any culture, composition or product containing them in the manufacture of a product for the therapeutic or prophylactic treatment of human and animal diseases.

DETAILED DESCRIPTION OF THE INVENTION

As mentioned above, the present invention provides a method of selection of new bacterial strains consisting in the ability of these strains to survive in breast milk and/or amniotic fluid, and by their ability to be transferred to breast milk and/or amniotic fluid after oral intake, which ensures the special characteristics of the selected strains obtained with it. Thus, the main aspect of the present invention is defined as a method for the selection of probiotic microbial strains, comprising the following steps:
 a. selecting for non-pathogenic strains which are capable of surviving in breast milk and/or amniotic fluid, and
 b. selecting for non-pathogenic strains which are able to be transferred to breast milk and/or amniotic fluid after oral intake in healthy individuals without colonizing other internal organs except mucousas.

According to a preferred embodiment of the invention, both breast milk and amniotic fluid are from human sources. The probiotic tested strains in the method of the invention can be any probiotic bacteria selected from, but not restricted to, the genera *Lactobacillus, Lactococcus, Leuconostoc, Enterococcus, Streptococcus* and *Bifidobacterium*. These probiotic strains are preferably obtained from breast milk, feces of breastfed babies or amniotic fluid, most preferably from human samples. Further details of the method of the invention are given below in "Method and Examples".

In a further aspect, the present invention provides any bacterial strain selected by the method of the invention. Some of these new bacterial strains which exhibit a number of characteristics which render them beneficial to human health, and in particular in the prophylaxis or treatment against digestive, infective, neuro-degenerative and other immune related diseases such as allergies or inflammatory diseases, have been deposited according to the Budapest Agreement at the CECT—Colección Española de Cultivos Tipo—, Valencia (Spain) on Jun. 11, 2002. These bacterial strains and their characteristics are:

CECT5711: (*Lactobacillus coryniformis*), said bacteria being obtained from goat cheese, selected by the proposed process, and characterized by the RAPD profile showed in FIG. 3 and the features described in Table I, II and VIII.

CECT5713: (*Lactobacillus salivarius* subsp. *salivarius*), said bacteria being obtained from human breast-fed baby feces, selected by the proposed process, and characterized by the RAPD profile showed in FIG. 3 and the features described in Table I, II and to VIII.

CECT5714: (*Lactobacillus gasseri*, formerly *L. acidophilus*), said bacteria being obtained from human breast milk, said bacteria being obtained also in human amniotic fluid, selected by the proposed process, and characterized by the RAPD profile showed in FIG. 3 and the features described in Table I, II and VIII.

CECT5715: (*Lactobacillus gasseri*), said bacteria being obtained from human breast milk, detected also in human amniotic fluid, selected by the proposed process, and characterized by the RAPD profile showed in FIG. 3 and the features described in Table I, II and VIII.

CECT5716: (*Lactobacillus fermentum*), said bacteria being obtained from human breast milk, selected by the proposed process, and characterized by the RAPD profile showed in FIG. 3 and the features described in Table I, II and VIII.

Moreover we have also confirmed that by applying the method of the invention, it is possible to select new specific strains as the mentioned above. In this sense, we have compared genetic (RAPD profiles) and biochemical aspects such as fermentation capabilities (API profiles), enzymatic potential (APIZYM profiles) and antibiotic resistance of the selected strains with other strains of the same species deposited in several culture collections (namely CECT, ATCC, LMG, NCFB, etc. . . . ). Accordingly, we have established that these new strains are different from those previously reported.

To our knowledge, this is the first time that an experimental laboratory has observed that it is possible to obtain non-pathogenic bacterial microorganisms present in normal mammal breast milk or amniotic fluid, that exists a transfer of non-pathogenic bacterial strains to breast milk and amniotic fluid after oral intake, and that these microbial organisms are not pathogenic strains that could act as probiotic bacterial strains and thus, beneficially affect not only the subject who ingest them but also to the fetus or breast feeding infant. For this reason, a further aspect of the present invention refers to the use of the mammal breast milk and amniotic fluid as new sources of bacterial microorganisms having the ability to be used as probiotic strains, the strains obtained from them, and the use thereof. The breast milk and amniotic fluid are preferably human.

It is also an aspect of the invention comprising any of the bacterial strains of the invention together with at least another bacterial strain. In this regard, this invention refers to biological pure cultures of each of the strains, or mixtures among them or with other bacterial strains. Thus, said aspect of this invention is the production of different compositions comprising at least a strain or a mixture of the strains of the invention. According to this aspect, the invention provides a composition comprising at least one of the bacterial strains of the invention, i.e., one of the strains mentioned above or any bacterial strain selected by the method of the invention, where the composition comprises preferably from 2 to 6 strains, more preferably from 2 to 4 strains, most preferably from 2 to 3 strains, and where each of the strains is present in the composition in a proportion from 0.1% to 99.9%, preferably from 1% to 99%, more preferably from 10% to 90%. In a preferred embodiment, the composition comprises at least one of the bacterial strains of the invention together with another strain or mixture of strains where the mixture comprises preferably from 2 to 6 strains, more preferably from 2 to 4 strains, most preferably from 2 to 3 strains and where each of the strains is present in the composition in a proportion from 0.1% to 99.9%, preferably from 1% to 99%, more preferably from 10% to 90%.

The compositions of the invention are preferably (no creo que sea preferible que sean asi, simplemente lo pueden ser) in a lyophilised form, in a frost form or even dead.

In a further aspect, the present invention provides a composition obtainable from the supernatant of a culture of a bacterial strain of the invention, or from any composition of the invention. In a preferred embodiment the composition is obtainable by extraction of a culture of any of the bacterial strains of the invention or from a composition of the invention.

The supernatant of a culture of a *Lactobacillus* strain of the present invention may be used for preparing an administrable support. The supernatant may be used as such or may well be dried under conditions that do not destroy the metabolic compounds secreted or produced by the microorganisms into the liquid medium, such as e.g. freeze drying. The present invention also refers to the use of enzymes obtained from these probiotic strains and their use in the production of protein hydrolysates or metabolites. The present invention also refers to compositions of the strains of this invention in a lyophilized form, freeze dried or inactivated (dead bacteria) by conventional methods. Thus yet in another aspect, the invention provides a product obtainable from the metabolic activity of any of the strains of the invention, of a culture of ay strain of the invention or of a composition according to the present invention, wherein the product is preferably an enzyme.

A further aspect of the invention consists in a food product comprising support material and at least one strain according to the invention, a culture, a composition or a product according to the present invention. Preferably, the support material is a food composition selected from milk, yoghourt, curd, cheese, fermented milks, milk based fermented products, meat based fermented products, fermented cereals based products, milk based powders, cereal based powders, infant formulae, clinical nutrition formula, ice-creams, juices, flours, bread, cakes, sugar, candies or chewing-gums. In a preferred embodiment, the microbial strain according to the instant invention is contained in the support material in an amount from about $10^5$ cfu/g to about $10^{12}$ cfu/g support material, preferably from about $10^6$ cfu/g to about $10^{11}$ cfu/g support material, more preferably from about $10^6$ cfu/g to about $10^{10}$ cfu/g support material.

For the purpose of the present invention the abbreviation cfu shall designate a "colony forming unit" that is defined as the number of bacterial cells as revealed by microbiological counts on agar plates.

In another aspect the present invention provides pharmaceutical compositions comprising at least one strain according to the invention, a culture, a composition or a product according to the invention and pharmaceutically acceptable excipients. The required dosage amount in the food or pharmaceutical composition described before will vary according to the nature of the disorder or the proposed use of the composition, whether used prophylactically or therapeutically and the type of organism involved. For preparing a food composition according to the present invention at least one of the *Lactobacillus* strains of the present invention is incorporated in a suitable support, in n amount of from $10^5$ cfu/g to about $10^{14}$ cfu/g support material, preferably from about $10^6$ cfu/g to about $10^{13}$ cfu/g support material, more preferably from about 107 cfu/g to about $10^{12}$ cfu/g support material.

The pharmaceutical preparations can be prepared in forms of tablets, capsules, liquid bacterial suspensions, dried oral supplements, wet oral supplements, dry tube feeding or a wet tube feeding.

Nevertheless, the activity of the new microorganisms in the individual is naturally dose dependent. That is, the higher the number of the novel microorganisms that are incorporated by means of ingestion or administration of the above food material or the pharmaceutical composition, the higher protective and/or therapeutic activity of the microorganisms. Since the microorganisms of this invention are not detrimental to man and animals and have eventually been isolated from baby feces, food or human breast milk or amniotic fluid, a high amount thereof may be incorporated so that essentially a high proportion of the individual's mucosa will be colonized by the novel microorganisms.

Preferably, the subject in need of treatment is selected from the group consisting of individuals who suffer the disorder or having risk to suffer the selected disorder, namely infection, allergy, inflammation, etc. However, it will be recognized that the present treatments are suitably employed in prophylaxis of those disorders in any subject.

Moreover, due to the ability of the selected strains to be transferred to and survive in breast milk and/or amniotic fluid, the subjects in need of treatment could not only be those who intake directly the selected strains but also the fetus or breast feeding babies.

Preferably the probiotic, or the probiotic-containing composition, is directed to the oral, gastric or to the intestinal mucosal surface; however, it could also be directed to nasopharingeal, respiratory, genitourinary or glandular mucosa, and it could be administered to human and animals by an oral, rectal, topical, urethral or vaginal route.

Further, the probiotics of the present invention may be used in conjunction with other treatments, to enhance or assist in their efficacy.

Many people have a disturbed intestinal microflora, that is, the balance between useful and harmful intestinal bacteria is disturbed. A number of factors, among others stress, the presence of bile salts, and specially diet, influence the bacterial flora. In these situations the fermentation process could be disturbed and the number of useful bacteria be reduced, the consequence would be that the colon mucosa withers away and ceases to function at the same time as the potentially malignant bacteria rapidly grow in number. For this reason, one aspect of this invention is the use of probiotics as prophylactic or therapeutic treatment of chronic or acute infection, or of undesirable microbial colonization, of a mucosal surface, comprising the administration of an effective amount of a probiotic, or a probiotic-containing composition, to a subject in need thereof.

The compositions of the present invention can also be used effectively in the treatment of acute and chronic viral infections. In particular, the treatment of chronic Epstein-Barr virus, cytomegalovirus and other herpes-type virus infection, which are ubiquitous in the population and are associated with a decrease on the immune survillance.

Another embodiment of the invention is the use of the probiotic bacteria of this invention for the prophylactic or therapeutic treatment of diarrhea, independently whether this disorder is due to the presence of a parasitic infestation and/or bacterial or viral infection, the treatment with antibiotics or quimio- or radio-therapy or to dietary or physical complications.

The present invention also relates to the use of the stated probiotics for the prevention and treatment of temporarily reduced immune activity levels and normalizing immune activity levels that are depressed in comparison with what may be considered normal, such as that produced in aging or in healthy individuals who are subject to intense exertion or in general to a great physiological strain.

Moreover, through modulation of the immune response and the balance between Th1 and Th2 cytokines, the probiotics of the invention could also be used for the prophylactic or therapeutic treatment of allergy and disorders related with the development of tolerance against ingested proteins.

Another embodiment of the invention is the use of the probiotics of this invention for the prophylactic or therapeutic treatment of chronic inflammatory disorders such as, but not restricted to, psoriasis, sarcoidosis, atherosclerosis, inflammatory bowel disease, due to the ability of some of the probiotic strains to reduce the production of pro-inflammatory cytokines by activated macrophages.

The present invention also relates to the use of the strains stated in this invention for the prophylactic or therapeutic treatment of some cancer types. This use of the strains is based on the described effects of some lactic acid bacteria counteracting cancer due to their effects in the inhibition of carcinogenic toxins in the intestines such as nitrosamines but also for the effect of this probiotics in the modulation of the natural immune defense.

Finally, the present invention also refers to the use of these probiotic strains for the prophylactic or therapeutic treatment of neuro-degenerative diseases due to the hypocholesterolemic and the modulation of the oxidative stress effect of some strains of probiotics. Both situations have been related as risk factors for the development of neuro-degeneratives diseases such as Parkinson or Alzheimer. Moreover, it has also been described that commensal bacteria are able to deaminate L-tryptophan producing indole-3-propionic acid which is a potent neuroprotective agent.

We have also tested the potential of the strains selected by the selection method of the present invention, analyzing the probiotic properties of the selected strains using conventional criteria. In this sense we have studied the following aspects: a) Acid and bile stability, because the bacteria are mainly ingested and must pass through the acidic environment of the stomach as well as the bile-containing small intestine, and they must be able to survive in these conditions; b) Adherence to intestinal mucosa, because this property permits the bacteria to colonize and become established in the gastrointestinal tract; c) Fermentative and high proliferative capabilities, to enhance the establishment in the mucosa; d) Resistance to antibiotics, because it could be necessary for some indications; e) Reduction of pH (lactic acid production) and production of antimicrobial metabolites by the strains of the invention, since it can help them to form a protective barrier to pathogens within the gastrointestinal tract; f) Immunomodulatory capabilities.

The following methods and examples illustrate the invention.

METHODS AND EXAMPLES

Example 1

New Method of Selection of Probiotic Strains

We have developed a novel method of selection of new bacterial strains consisting in the ability of these strains to survive in breast milk and/or amniotic fluid, and by their ability to be transferred to breast milk and/or amniotic fluid after oral intake. The rationale of this novel method described in the present invention is that ensures special characteristics of the selected strains obtained with it, since the bacterial strains obtained have implicitly most of the characteristics attributed to a potential probiotic strain, namely good resistance to digestion process and the ability of gut colonization, but also a more natural human origin, safety aspects, and the ability to colonize and regulate some human niches other than the gut. Moreover, these new strains have been obtained from different sources apart from feces, such as goat cheese and from human breast milk and amniotic fluid.

Example 1a

Resistance to Human Fluids

Figure 1:
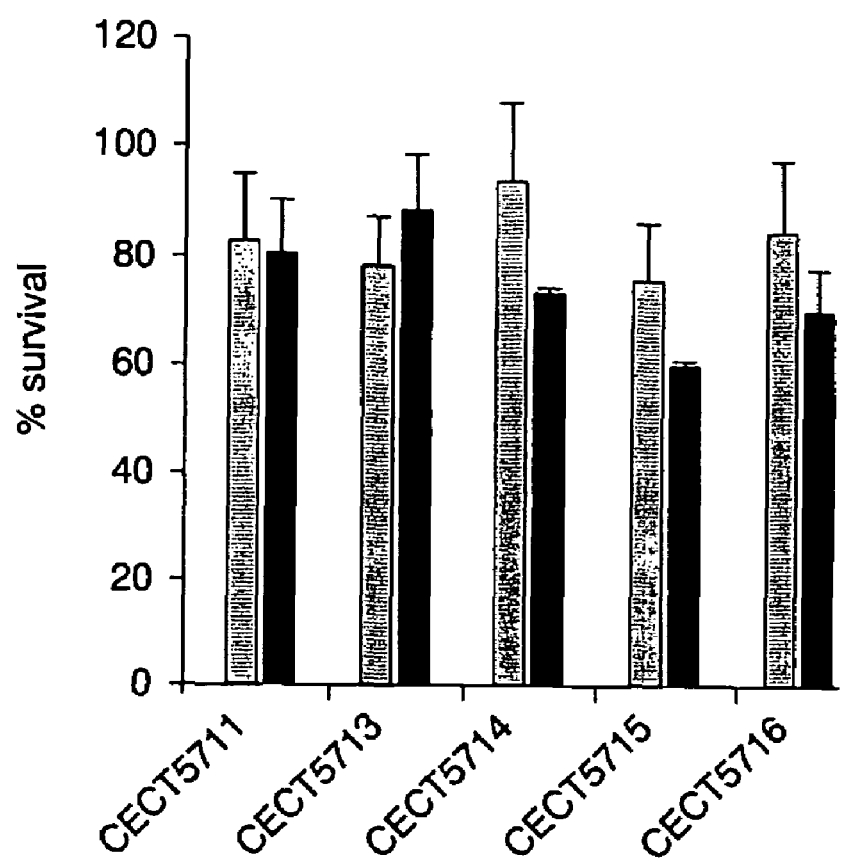
FIG. 1. Screening method: Survival of bacteria into breast milk and amniotic fluid.

Colonies isolated from different sources were checked by their ability to survive in human breast milk and also in human amniotic fluid. To analyze the survival rate of the probiotic strains of this invention, $10^8$ cfu of each bacteria were cultured in 1 ml of human breast milk or human amniotic fluid for 60 minutes in anaerobic conditions at 37° C. The survival was calculated by MRS agar plating of serial dilutions and compared to the number of colonies obtained in control conditions (MRS broth pH 6.2). Plates were cultured 16-18 hours at 37° C. in anaerobic conditions. The experiment was repeated three times. Strains were considered resistant when the survival at least in one of the human fluids was higher than 75% compared with the control conditions (FIG. 1).

Example 1b

Transfer to Human Fluids

The second criteria in the selection process described in the present invention is that bacteria should be able to be transferred to breast milk and/or amniotic fluid after oral intake. In order to test this capability, the putative strains were genetically labeled, as described latter, and orally administered to pregnant mice as animal model. Transfer of bacteria was analyzed by PCR screening of the colonies obtained from the amniotic fluid and from the gut of breastfed mice.

Labeling of Bacteria:

Three primer couples were employed to obtain three different PCR fragments (F159: 159 bp, F189: 189 pb, and F228: 228 bp, respectively). The three fragments included the junction between the 35S rRNA promoter of the Cauliflower Mosaic Virus (CaMV) and the 5-enolpyruvylshikimate-3-phosphate synthase (EPSPS) gene from *Agrobacterium tumefaciens*. The primers were designed from the artificial sequence present in Roundup Ready soya (EMBL accession number: AX033493). BamHI sites were added to the 5'-tails of all the primers to facilitate the cloning of the PCR fragments. Once obtained, the PCR products were purified using the QIAquick PCR purification kit (Qiagen), digested with BamHI, and ligated into pTG262, a plasmid that confers resistance to Chloramphenicol (Cm). Subsequently, these plasmids were individually introduced into the selected strains by electroporation following conventional protocols. Identity of the transformants was confirmed by PCR (FIG. 2A).

Transfer of Bacteria:

Four pregnant Balb/c mice were orally inoculated with $10^8$ cfu of genetically-labelled strains vehiculated in 200 µl of milk every two days from two weeks before labor. Just before labor, amniotic fluid was aseptically collected from two of the mice, and cultured on MRS agar plates. The other two pregnant mice finalized gestation. The transfer of the genetically labeled bacteria to breast milk was analyzed by comparison of the bacteria isolated from the neonate's gut just before and after first lactation. All the plates were incubated for 24 h at 37° C. under anaerobic conditions. For each sample obtained, 52 colonies were randomly selected among those that grew on the MRS plates and subcultured on Cm-MRS plates. Finally, to detect the genetically-labeled colonies among the Cm-resistant colonies, PCR analyses were performed using DNA from the Cm-resistant colonies as template (FIG. 2B). Transfer was considered positive when at least two PCR-positive colonies could be detected in at least one of the samples.

The bacterial strains selected by the method described in the present invention were further tested in order to establish their singularity and their probiotic properties as described in the examples 3 and 4.

Example 1c

Isolation of Lactic Acid Bacteria

The bacterial strains that have been submitted to the selection method described in the present invention have been obtained from different sources apart from feces, such as goat cheese and from human breast milk and amniotic fluid. This isolation process have been performed as described above:

Isolation From Human Breast Milk:

Two milliliter samples of human breast milk was collected aseptically from a 35 year-old woman (15 days after delivery). In order to isolate bacterial strains from this sample, serial dilutions of 0.1 ml in peptone water were plated on MRS (pH 6.2), MRS (pH 5.5), APT, RCM, LM17, GM17 and Elliker agar plates at 37° C. in both aerobic and anaerobic conditions for 24-48 hours. From about 740 colonies in total, 74 colonies (10%) that included at least two colonies of the appreciated different morphologies were selected and further cultured in MRS agar at 37° C. in anaerobic conditions and tested according to the proposed method. Two of the colonies obtained from this sample were able to fulfill the defined criteria.

The selected breast milk-derived *Lactobacillus gasseri* CECT5714 and *Lactobacillus fermentum* CECT5716 were originally isolated from the MRS (pH 6.2) agar plates cultured in aerobic conditions, whereas the *Lactobacillus gasseri* CECT5715 was isolated from the APT agar plates cultured in anaerobic conditions.

Isolation From Human Amniotic Fluid:

Isolation of bacterial strains from human amniotic fluid was performed by dilution of 2 ml of human amniotic fluid collected aseptically by the clinical staff during labor from two volunteers. Serial dilutions of 0.1 ml in peptone water were plated on MRS (pH 6.2), MRS (pH 5.5), APT, RCM, LM17, GM17 and Elliker agar plates at 37° C. in both aerobic and anaerobic conditions for 24-48 hours. From about 400 colonies in total, 40 colonies (10%) that included at least two colonies of the appreciated different morphologies were selected and further cultured in MRS agar at 37° C. in anaerobic conditions and tested according to the proposed method.

The two strains selected from this source were identical to those previously selected from human breast milk, namely *Lactobacillus gasseri* CECT5714 and CECT5715.

Isolation From Food Products (Goat Cheese):

Isolation of bacterial strains from food products was carried out by homogeneization in peptone water of 20 g of a central part of the food product collected aseptically. 0.1 ml of serial dilutions were plated in MRS agar (Oxoid) plates and RCM agar (Oxoid) plates and cultured in both aerobic and anaerobic conditions at 32° C. for 48 hours. From more than 500 colonies in total, 5 colonies of each condition were selected and further cultured in MRS agar at 37° C. in anaerobic conditions. These colonies were tested according to the proposed method. Only one of the colonies was able to fulfill the defined criteria. The selected cheese-derived colony *Lactobacillus coryniformis* CECT5711 was originally isolated from MRS agar plates cultured in aerobic conditions.

Isolation From Human Breast-Fed Baby Feces:

Isolation of bacterial strains from human feces was performed by homogenization of 2 g of feces collected aseptically from three independent babies (15-45 day old) in peptone water. 0.1 ml of serial dilutions were plated on MRS (pH 6.2), MRS (pH 5.5), APT, RCM, LM17, GM17 and Elliker agar plates at 37° C. in both aerobic and anaerobic conditions for 24-48 hours. From about 670 colonies in total, 67 colonies (10%) that included at least two colonies of the appreciated different morphologies were selected and further cultured in MRS agar at 37° C. in anaerobic conditions and tested according to the proposed method. Only one of the colonies was able to fulfill the defined criteria.

The selected baby feces-derived *Lactobacillus salivarius* subsp. *salivarius* CECT5713 was originally isolated from the MRS (pH 6.2) agar plates cultured in aerobic conditions.

Example 2

Physiological and Genetic Characterization

The phenotype of each selected bacterial strain grown on MRS media (agar or broth) at 37° C. in anaerobic conditions was as described in Table I:

TABLE I

Phenotypic characteristics of the different probiotic strains of the invention. The phenotypic characteristics of the different probiotic strains of the invention were compared to that observed in known commercial probiotic strains (*Lactobacillus rhamnosus* LGG from Valio, *Lactobacillus johnsonii* La1 from Nestlé and *Lactobacillus casei immunitas* from Danone).

| TEST | CECT5711 | CECT5713 | CECT5714 | CECT5715 | CECT5716 | LGG | LA1 | LC |
|---|---|---|---|---|---|---|---|---|
| Origen | cheese | feces | breast milk | breast milk | breast milk | feces | feces | feces |
| Gram | + | + | + | + | + | + | + | + |
| catalase | − | − | − | − | − | − | − | − |
| oxidase | − | − | − | − | − | − | − | − |
| morphology | rod | rod | rod | rod | rod | rod | rod | small rod |
| size (µm) | 1 × 1.5-4 | 0.9 × 1.5-3 | 0.9 × 2-4 | 1× 2-10 | 1 × 1.5-3 | 1 × 2-4 | 0.9 × 1.5-3.5 | 0.9 × 1.5-2 |
| motility | nonmotile | nonmotile | nonmotile | nonmotile | nonmotile | nonmotile | nonmotile | nonmotile |
| agregation | single/pairs | single/pairs | single/pairs | single/pairs | single/pairs | long chains | single/pairs | single-pairs |

For the identification of the selected probiotic strains a fermentation API 50CH (BioMerieux) analysis at 37° C. in anaerobic conditions for 24 and 48 hours was carried out following the specified instructions indicated by the manufacturer. The results after 24 hours of culture are summarized in Table II. A positive fermentable substrate is that with a value higher than 3.

TABLE II

Fermentation pattern of the different probiotic strains of the invention. The fermentation capabilities of the different probiotic strains of the invention were compared to that observed in some commercial probiotic strains (*Lactobacillus rhamnosus* LGG from Valio, *Lactobacillus johnsonii* La1 from Nestle and *Lactobacillus casei immunitas* from Danone) using the API 5OCH method (BioMerieux). Positive fermentable substrates are indicated in grey.

| TEST | 5711 | 5713 | 5714 | 5715 | 5716 | LGG | LA1 | L. casei |
|---|---|---|---|---|---|---|---|---|
| Glycerol | 0 | 0 | 0 | 0 | 0 | 0 | 0 | 0 |
| Erythritol | 0 | 0 | 0 | 0 | 0 | 0 | 0 | 0 |
| D-Arabinose | 0 | 0 | 0 | 0 | 0 | 3 | 0 | 0 |
| L-Arabinose | 0 | 3 | 0 | 4 | 4 | 0 | 0 | 5 |
| Ribose | 0 | 4 | 0 | 4 | 4 | 0 | 0 | 5 |
| D-Xylose | 0 | 0 | 0 | 0 | 0 | 0 | 0 | 0 |
| L-Xylose | 0 | 0 | 0 | 0 | 0 | 0 | 0 | 0 |
| Adonitol | 0 | 0 | 0 | 0 | 0 | 0 | 0 | 0 |
| β Methyl-xyloside | 0 | 0 | 0 | 0 | 0 | 0 | 0 | 0 |
| Galactose | 4 | 5 | 4 | 5 | 5 | 5 | 4 | 5 |
| D-Glucose | 5 | 5 | 5 | 5 | 5 | 5 | 5 | 5 |
| D-Fructose | 5 | 5 | 5 | 5 | 5 | 5 | 5 | 5 |
| D-Mannose | 5 | 5 | 5 | 5 | 3 | 5 | 3 | 5 |
| L-Sorbose | 0 | 0 | 0 | 0 | 0 | 0 | 0 | 0 |
| Rhamnose | 0 | 0 | 0 | 0 | 0 | 0 | 0 | 3 |
| Dulcitol | 0 | 0 | 0 | 0 | 0 | 5 | 0 | 0 |
| Inositol | 0 | 0 | 0 | 0 | 0 | 1 | 0 | 0 |
| Mannitol | 5 | 5 | 0 | 3 | 0 | 5 | 0 | 4 |
| Sorbitol | 0 | 5 | 0 | 0 | 0 | 5 | 0 | 1 |
| α Methyl-D-mannoside | 0 | 0 | 0 | 0 | 0 | 0 | 0 | 0 |

TABLE II-continued

Fermentation pattern of the different probiotic strains of the invention. The fermentation capabilities of the different probiotic strains of the invention were compared to that observed in some commercial probiotic strains (*Lactobacillus rhamnosus* LGG from Valio, *Lactobacillus johnsonii* La1 from Nestle and *Lactobacillus casei immunitas* from Danone) using the API 50CH method (BioMerieux). Positive fermentable substrates are indicated in grey.

| | | | | | | | | | |
|---|---|---|---|---|---|---|---|---|---|
| α Methyl-D-glucoside | 0 | 0 | 0 | 0 | 0 | | 0 | 0 | 0 |
| N Acethyl glucosamine | 5 | 5 | 4 | 5 | 0 | | 5 | 4 | 5 |
| Amygdaline | 0 | 0 | 0 | 5 | 0 | | 1 | 0 | 1 |
| Arbutine | 0 | 4 | 5 | 5 | 4 | | 4 | 0 | 4 |
| Esculine | 0 | 5 | 5 | 5 | 0 | | 5 | 5 | 5 |
| Salicine | 0 | 3 | 5 | 5 | 0 | | 5 | 1 | 4 |
| Cellobiose | 0 | 4 | 5 | 5 | 0 | | 5 | 5 | 5 |
| Maltose | 0 | 5 | 5 | 5 | 5 | | 0 | 1 | 5 |
| Lactose | 5 | 5 | 0 | 4 | 5 | | 0 | 5 | 5 |
| Melibiose | 0 | 5 | 0 | 0 | 5 | | 0 | 0 | 0 |
| Saccharose | 5 | 5 | 5 | 5 | 5 | | 1 | 5 | 5 |
| Trehalose | 0 | 5 | 5 | 5 | 0 | | 5 | 4 | 4 |
| Inuline | 0 | 0 | 0 | 0 | 0 | | 0 | 0 | 0 |
| Melezitose | 0 | 0 | 0 | 0 | 0 | | 2 | 0 | 0 |
| D-Raffinose | 0 | 5 | 0 | 0 | 5 | | 0 | 4 | 0 |
| Amidon | 0 | 0 | 3 | 5 | 0 | | 0 | 0 | 1 |
| Glycogene | 0 | 0 | 0 | 0 | 0 | | 0 | 0 | 0 |
| Xylitol | 0 | 0 | 0 | 0 | 0 | | 0 | 0 | 0 |
| β Gentiobiose | 0 | 0 | 5 | 5 | 0 | | 2 | 5 | 4 |
| D-Turanose | 0 | 0 | 0 | 0 | 0 | | 0 | 0 | 0 |
| D-Lyxose | 0 | 0 | 0 | 0 | 0 | | 0 | 0 | 0 |
| D-Tagatose | 0 | 0 | 5 | 5 | 0 | | 5 | 3 | 3 |
| D-Fucose | 0 | 0 | 0 | 0 | 0 | | 0 | 0 | 0 |
| L-Fucose | 0 | 0 | 0 | 0 | 0 | | 4 | 0 | 0 |
| D-Arabitol | 0 | 0 | 0 | 0 | 0 | | 0 | 0 | 0 |
| L-Aribitol | 0 | 0 | 0 | 0 | 0 | | 0 | 0 | 0 |
| Gluconate | 0 | 1 | 0 | 1 | 1 | | 3 | 0 | 3 |
| 2 ceto-gluconate | 0 | 0 | 0 | 0 | 0 | | 0 | 0 | 0 |
| 5 ceto-gluconate | 0 | 0 | 0 | 0 | 0 | | 1 | 0 | 0 |

The selected bacterial strains were taxonomically classified according to their SDS-PAGE 1D protein profiling and 16S rDNA sequence by BCCM/LMG (Belgium) and/or NIZO Food Research (The Netherlands), respectively. The results obtained from these tests lead to the taxonomical classification of the bacterial strains as indicated above. With this classification the bacterial strains of the invention were deposited according to the Budapest Agreement at the CECT—Colección Española de Cultivos Tipo—, Valencia (Spain) on Jun. 11, 2002 and with the following accession numbers:

*Lactobacillus coryniformis*: CECT5711
*Lactobacillus salivarius* subsp. *salivarius*: CECT5713
*Lactobacillus acidophilus*: CECT5714
*Lactobacillus gasseri*: CECT5715
*Lactobacillus fermentum*: CECT5716

Example 3

Singularity of the Selected Strains

Although the analysis of the SDS-PAGE 1D protein profiling and 16S rDNA sequence performed in example 2 are suitable methods to define bacterial species, they have not enough specifity to discriminate between different strains of the same bacterial species. For this reason, RAPD-PCR analysis of the strains was performed using two different lactobacilli specific primers (ArgDei and OPL5). For the Randomly Amplified Polymorphic DNA (RAPD)-PCR analysis, genomic DNA was isolated from 10 ml of overnight MRS cultures using the DNeasy tissue kit (Qiagen) and following the protocol recommended by the supplier for isolation of genomic DNA from Gram-positive bacteria. Total DNA was used in subsequent PCR amplifications carried out in a Techne DNA Thermal Cycler. PCR amplifications were performed using either primer OPL5 (5'-ACGCAGGCAC-3'), or ArgDei (5'-ACCYTRGAAGGYGGYGATGTB-3'). Five □l of the PCR mixtures were analyzed on a 1.2% (wt/vol) agarose (Sigma) gel with ethidium bromide staining. A 100-bp ladder (Invitrogen) was used as a molecular weight standard. Gels were run for approximately 1 h at 100 V, and the DNA was visualized and analyzed in a gel documentation system (Gel Doc 2000, Bio-Rad), using the Diversity Database software package (Bio-Rad).The results are showed in FIG. 3.

Moreover, in order to test the singularity of the bacterial strains selected with this new process and compare them with strains obtained by other selection criteria but that had been previously assigned to the same species. These probiotic strains were obtained from several culture collections such as CECT, ATCC, LMG or DSM and described in Table III.

TABLE III

Probiotic strains used for testing the singularity of the probiotics included in this invention.

*Lactobacillus coryniformis*

| | |
|---|---|
| DSM 20005: | *Lactobacillus coryniformis* subsp. *torquens* |
| DSM 20007: | *Lactobacillus coryniformis* subsp. *coryniformis* |
| CECT 982: | *Lactobacillus coryniformis* subsp. *coryniformis* |
| CECT 4129: | *Lactobacillus coryniformis* subsp. *torquens* |

TABLE III-continued

Probiotic strains used for testing the singularity of the probiotics included in this invention.

*Lactobacillus fermentum*

| | |
|---|---|
| LMG 8900: | *Lactobacillus fermentum* = ATCC 11976 |
| LMG 17551: | *Lactobacillus fermentum* = ATCC 23271 |
| CECT 285: | *Lactobacillus fermentum* = ATCC 9338 |
| CECT 4007: | *Lactobacillus fermentum* = ATCC 14931 |

*Lactobacillus gasseri*

| | |
|---|---|
| LMG 11413: | *Lactobacillus gasseri* |
| LMG 13047: | *Lactobacillus gasseri* = ATCC 19992 |
| LMG 13134: | *Lactobacillus gasseri* = ATCC 9857 |
| LMG 18176: | *Lactobacillus gasseri* |
| LMG 18194: | *Lactobacillus gasseri* |
| CECT 4479: | *Lactobacillus gasseri* |

*Lactobacillus salivarius*

| | |
|---|---|
| DSM 20492: | *Lactobacillus salivarius* |
| CECT 4062: | *Lactobacillus salivarius* |
| CECT 4063: | *Lactobacillus salivarius* |

All the selected strains included in this invention were compared with the strains described in Table III regarding their RAPD-PCR profiles using two different primers, results of this analysis (FIG. 4) shown that the selected strains included in this invention are different to those previously described. Moreover, we extended our results and compared not only genetic characteristics but also biochemical aspects of the selected strains with those strains described in Table III. In this sense, we performed API analyses (BioMerieux) (Table IV), APIZYM analyses (BioMerieux) (Table V) and antibiotic resistance as described in example 5g (Table VI). The activities that differ to that observed with the strains of this invention has been indicated in grey.

TABLE IV

Comparison of API profiles of the selected bacteria using the method described in this invention with other bacteria of the same species

| | TEST | 5711 | 4129 | 982 | 2007 | 2005 | 5713 | 4983 | 4162 | 20492 | 5714 | 11413 | 18194 | 4479 | 18176 | 13047 |
|---|---|---|---|---|---|---|---|---|---|---|---|---|---|---|---|---|
| | Glycerol | 0 | 0 | 0 | 0 | 0 | 0 | 0 | 0 | 1 | 0 | 0 | 0 | 0 | 0 | 0 |
| *L. fermentum* | Erythritol | 0 | 0 | 0 | 0 | 0 | 0 | 0 | 0 | 0 | 0 | 0 | 0 | 0 | 0 | 0 |
| | D-Arabinose | 0 | 0 | 0 | 0 | 0 | 0 | 0 | 0 | 0 | 0 | 0 | 0 | 0 | 0 | 0 |
| | L-Arabinose | 0 | 0 | 0 | 0 | 0 | 0 | 0 | 0 | 0 | 0 | 0 | 0 | 0 | 0 | 0 |
| | Ribose | 0 | 0 | 0 | 0 | 0 | 0 | 0 | 0 | 0 | 0 | 0 | 0 | 0 | 0 | 0 |
| | D-Xylose | 0 | 0 | 0 | 0 | 0 | 0 | 0 | 0 | 0 | 0 | 0 | 0 | 0 | 0 | 0 |
| | L-Xylose | 0 | 0 | 0 | 0 | 0 | 0 | 0 | 0 | 0 | 0 | 0 | 0 | 0 | 0 | 0 |
| | Adonitol | 0 | 0 | 0 | 0 | 0 | 0 | 0 | 0 | 0 | 0 | 0 | 0 | 0 | 0 | 0 |
| | β Methyl-xyloside | 0 | 0 | 0 | 0 | 0 | 0 | 0 | 0 | 0 | 0 | 0 | 0 | 0 | 0 | 0 |
| | Galactose | 5 | 5 | 5 | 5 | 5 | 5 | 5 | 5 | 5 | 5 | 5 | 5 | 5 | 5 | 5 |
| | D-Glucose | 5 | 5 | 5 | 5 | 5 | 5 | 5 | 5 | 5 | 5 | 5 | 5 | 5 | 5 | 5 |
| | D-Fructose | 5 | 5 | 5 | 5 | 5 | 5 | 5 | 5 | 5 | 5 | 5 | 5 | 5 | 5 | 5 |
| | D-Mannose | 5 | 5 | 5 | 5 | 5 | 5 | 5 | 5 | 5 | 5 | 5 | 5 | 5 | 5 | 5 |
| | L-Sorbose | 0 | 0 | 0 | 0 | 0 | 0 | 0 | 0 | 0 | 0 | 0 | 0 | 0 | 0 | 0 |
| | Rhamnose | 0 | 0 | 0 | 0 | 0 | 0 | 0 | 0 | 0 | 0 | 0 | 0 | 0 | 0 | 0 |
| *L. gasseri* | Dulcitol | 0 | 0 | 0 | 5 | 0 | 0 | 0 | 0 | 0 | 0 | 0 | 0 | 0 | 0 | 0 |
| | Inositol | 0 | 0 | 0 | 0 | 0 | 0 | 0 | 0 | 0 | 0 | 0 | 0 | 0 | 0 | 0 |
| | Mannitol | 5 | 5 | 5 | 5 | 5 | 5 | 5 | 5 | 5 | 0 | 0 | 0 | 0 | 0 | 0 |
| | Sorbitol | 0 | 0 | 0 | 0 | 0 | 5 | 5 | 5 | 5 | 0 | 0 | 0 | 0 | 0 | 0 |
| | α Methyl-D-mannoside | 0 | 0 | 0 | 0 | 0 | 0 | 0 | 0 | 0 | 0 | 0 | 0 | 0 | 0 | 0 |
| | α Methyl-D-glucoside | 0 | 0 | 0 | 0 | 0 | 0 | 0 | 0 | 0 | 0 | 0 | 0 | 0 | 0 | 0 |

TABLE IV-continued

Comparison of API profiles of the selected bacteria using the method described in this invention with other bacteria of the same species

| | | | | | | | | | | | | | | | |
|---|---|---|---|---|---|---|---|---|---|---|---|---|---|---|---|
| N-Acethyl glucosamine | 4 | 4 | 5 | 5 | 5 | 5 | 5 | 5 | 5 | 4 | 5 | 5 | 5 | 5 | 5 |
| Amygdaline | 0 | 0 | 0 | 0 | 0 | 0 | 0 | 0 | 0 | 5 | 5 |  | 5 | 5 |  |
| Arbutine | 0 | 0 | 0 | 0 | 0 | 0 | 0 |  | 0 | 5 | 5 |  | 5 | 5 | 4 |
| Esculine | 0 | 0 | 0 | 0 | 0 | 0 | 0 | 0 | 0 | 5 | 5 | 5 | 5 | 5 | 5 |
| Salicine | 0 | 0 |  | 0 | 0 | 0 | 0 |  | 0 | 5 | 5 | 5 | 5 | 5 | 3 |
| Cellobrose | 0 | 0 | 0 | 0 | 0 | 0 | 0 | 0 | 0 | 5 | 5 | 5 | 5 | 5 | 5 |
| Maltose | 4 | 5 |  | 5 | 5 | 5 | 5 | 5 | 5 | 5 | 5 | 5 | 5 | 5 | 5 |
| Lactose | 5 | 5 |  |  | 5 | 5 | 5 | 5 | 5 | 0 | 1 |  |  |  | 0 |
| Melibrose | 0 | 0 | 0 | 0 | 0 | 5 | 5 | 5 | 5 | 0 | 0 | 0 | 0 |  | 0 |
| Saccharose | 5 | 5 | 5 | 5 | 5 | 5 | 5 | 0 | 5 | 5 | 5 | 5 | 5 | 5 | 5 |
| Trehalose | 0 | 0 | 0 | 0 | 0 | 5 | 5 | 5 | 5 | 5 | 5 | 5 | 5 | 5 | 5 |
| Inuline | 0 | 0 | 0 | 0 | 0 | 0 | 0 | 0 | 0 | 0 | 0 | 0 | 0 | 0 | 0 |
| Melezilose | 0 | 0 | 0 | 0 | 0 | 0 | 0 | 0 | 1 | 0 | 0 | 0 | 0 | 0 | 0 |
| D-rabinose | 0 | 0 | 0 | 0 | 0 | 5 | 5 | 5 | 5 | 0 | 0 | 0 | 0 |  | 0 |
| Armidon | 0 | 0 | 0 | 0 | 0 | 0 | 0 | 0 | 0 | 3 |  |  |  | 3 | 3 |
| Glycogene | 0 | 0 | 0 | 0 | 0 | 0 | 0 | 0 | 0 | 0 | 0 | 4 | 0 | 0 | 0 |
| Xylitol | 0 | 0 | 0 | 0 | 0 | 0 | 0 | 0 | 1 | 0 | 0 | 0 | 0 | 0 | 0 |
| b-Gentiobrose | 0 | 0 | 0 | 0 | 0 | 0 | 0 | 0 | 1 | 5 | 5 | 5 | 5 | 5 | 5 |
| D-Turanose | 0 | 0 | 0 | 0 | 0 | 1 | 0 | 0 | 0 | 0 | 0 | 0 | 0 | 0 | 0 |
| D-Lycose | 0 | 0 | 0 | 0 | 0 | 0 | 0 | 0 | 0 | 0 | 0 | 0 | 0 | 0 | 0 |
| D-Tagatose | 0 | 0 | 0 | 0 | 0 | 0 | 0 | 0 | 0 | 5 | 5 | 3 | 5 | 5 | 5 |
| D-Fucose | 0 | 0 | 0 | 0 | 0 | 0 | 0 | 0 |  | 0 | 0 | 0 | 0 | 0 | 0 |
| L-Fucose | 0 | 0 | 0 | 0 | 0 | 0 | 0 | 0 |  | 0 | 0 | 0 | 0 | 0 | 4 |
| D-Arabinol | 0 | 0 | 0 | 0 | 0 | 0 | 0 |  | 0 | 0 | 0 | 0 | 0 | 0 | 0 |

| TEST | 5715 | 11413 | 18194 | 4479 | 18176 | 13047 | 5716 | 4007 | 285 | 17551 | 8900 |
|---|---|---|---|---|---|---|---|---|---|---|---|
| Glycerol | 0 | 0 | 0 | 0 | 0 | 0 | 0 | 0 | 0 | 0 | 0 |
| Erythritol | 0 | 0 | 0 | 0 | 0 | 0 | 0 | 0 | 0 | 0 | 0 |
| D-Arabinose | 4 |  |  |  |  |  | 0 | 0 | 0 | 0 | 0 |
| L-Arabinose | 4 |  |  |  |  |  | 4 | 0 | 0 | 0 | 5 |
| Ribose | 0 | 0 | 0 | 0 | 0 | 0 | 5 | 5 | 5 | 5 | 5 |
| D-Xylose | 0 | 0 | 0 | 0 | 0 | 0 | 0 | 0 |  |  | 0 |
| L-Xylose | 0 | 0 | 0 | 0 | 0 | 0 | 0 | 0 | 0 | 0 | 0 |
| Adonitol | 0 | 0 | 0 | 0 | 0 | 0 | 0 | 0 | 0 | 0 | 0 |
| β Methyl-xyloside | 0 | 0 | 0 | 0 | 0 | 0 | 0 | 0 | 0 | 0 | 0 |
| Galactose | 5 | 5 | 5 | 5 | 5 | 5 | 5 | 5 | 5 |  | 5 |
| D-Glucose | 5 | 5 | 5 | 5 | 5 | 5 | 5 | 5 | 5 | 5 | 5 |
| D-Fructose | 5 | 5 | 5 | 5 | 5 | 5 | 5 |  | 4 | 5 | 5 |
| D-Mannose | 5 | 5 | 5 | 5 | 5 | 5 | 3 |  | 4 | 3 | 3 |
| L-Sorbose | 0 | 0 |  | 0 | 0 | 0 | 0 | 0 | 0 | 0 | 0 |
| Rhamnose | 0 | 0 | 0 | 0 | 0 | 0 | 0 | 0 | 0 | 0 | 0 |
| Dulcitol | 0 | 0 |  | 0 | 0 | 0 | 0 | 0 | 0 | 0 | 0 |
| Inositol | 0 | 0 | 0 | 0 | 0 | 0 | 0 | 0 | 0 | 0 | 0 |
| Mannitol | 3 |  |  |  |  |  | 0 | 0 | 0 | 0 | 0 |
| Sorbitol | 0 | 0 | 0 | 0 | 5 | 5 | 0 | 0 | 0 | 0 | 0 |
| α Methyl-D-mannoside | 0 | 0 | 0 | 0 | 0 | 0 | 0 | 0 | 0 | 0 | 0 |
| α Methyl-D-glucoside | 0 | 0 | 0 | 0 | 0 | 0 | 0 | 0 | 0 | 0 | 0 |
| N-Acethyl glucosamine | 5 | 5 | 5 | 5 | 5 | 5 | 0 | 0 | 0 | 0 | 0 |
| Amygdaline | 5 | 5 |  | 5 | 5 |  | 0 | 0 | 0 | 0 | 0 |
| Arbutine | 5 | 5 |  | 5 | 5 | 4 | 4 |  |  |  |  |
| Esculine | 5 | 5 | 5 | 5 | 5 | 5 | 0 | 0 | 0 | 0 | 0 |
| Salicine | 5 | 5 | 5 | 5 | 5 | 5 | 0 | 0 | 0 | 0 | 0 |
| Cellobrose | 5 | 5 | 5 | 5 | 5 | 5 | 0 | 0 | 0 | 0 | 0 |
| Maltose | 5 | 5 | 5 | 5 | 5 | 5 | 4 | 5 | 5 | 5 | 5 |
| Lactose | 4 | 1 | 5 | 5 | 5 |  | 5 | 5 | 5 | 5 | 5 |
| Melibrose | 0 | 0 | 0 | 0 |  | 0 | 5 | 5 | 5 |  | 5 |
| Saccharose | 5 | 5 | 5 | 5 | 5 | 5 | 5 | 5 |  |  | 5 |
| Trehalose | 5 | 5 | 5 | 5 | 5 | 5 | 0 | 0 | 0 | 0 | 0 |
| Inuline | 0 | 0 | 0 | 0 | 0 | 0 | 0 | 0 | 0 | 0 | 0 |
| Melezilose | 0 | 0 | 0 | 0 | 0 | 0 | 0 | 0 | 0 | 0 | 0 |
| D-rabinose | 0 | 0 | 0 | 0 |  | 0 | 5 |  | 4 |  |  |
| Armidon | 5 |  |  | 5 |  |  | 0 | 0 | 0 | 0 | 0 |
| Glycogene | 0 | 0 | 0 | 0 | 0 | 0 | 0 | 0 | 0 | 0 | 0 |
| Xylitol | 0 | 0 | 0 | 0 | 0 | 0 | 0 | 0 | 0 | 0 | 0 |
| b-Gentiobrose | 5 | 5 | 5 | 5 | 5 | 5 | 0 | 0 | 0 | 0 | 0 |
| D-Turanose | 0 | 0 | 0 | 0 | 0 | 0 | 0 | 0 | 0 | 0 | 0 |
| D-Lycose | 0 | 0 | 0 | 0 | 0 | 0 | 0 | 0 | 0 | 0 | 0 |
| D-Tagatose | 5 | 5 |  | 5 | 5 | 5 | 0 | 0 | 0 | 0 | 0 |
| D-Fucose | 0 | 0 | 0 | 0 | 0 | 0 | 0 | 0 | 0 | 0 | 0 |
| L-Fucose | 0 | 0 | 0 | 0 | 0 | 0 | 0 | 0 | 0 | 0 | 0 |
| D-Arabinol | 0 | 0 | 0 | 0 | 0 | 0 | 0 | 0 | 0 | 0 | 0 |

Probiotic strains used were described in Table III. The activities that differ to that observed with the strains of this invention has been indicated in grey.

TABLE V

Comparison of APIZYM profiles of the selected bacteria using the method described in this invention with other bacteria of the same species.

| | Enzyme | DSM 20492 | CECT 4062 | CECT 4063 | CECT 5713 |
|---|---|---|---|---|---|
| *L. salivarius* | control | - | - | - | - |
| | alcalin phophatase | | | | - |
| | Esterase (C4) | 2 | 2 | | 3 |
| | Esterase lipase (C8) | | | | 3 |
| | Lipase (C14) | - | - | - | - |
| | Leucine arilamidase | + | + | + | + |
| | Valine arilamidase | - | | - | 1 |
| | Cystine arilamidase | | 4 | | 3 |
| | Trypsine | - | - | - | - |
| | α-quimiotrypsine | - | - | - | - |
| | Acid phosphatase | + | + | + | 4 |
| | Naftol-AS-BI-phosphohydrolase | | | | + |
| | α-galactosidase | | 3 | | 2 |
| | β-galactosidase | | | | - |
| | β-glucuronidase | - | - | - | - |
| | α-glucosidase | - | - | - | - |
| | β-glucosidase | - | - | - | - |
| | N-acethyl-β-glucosaminidases | - | - | - | - |
| | α-mannosidase | - | - | - | - |
| | α-frucosidase | - | - | - | - |

| | Enzyme | DSM 20005 | CECT 4129 | DSM 20007 | CECT 982 | CECT 5711 |
|---|---|---|---|---|---|---|
| *L. coryniformis* | control | - | - | - | - | - |
| | alcalin phophatase | 1 | 1 | - | - | - |
| | Esterase (C4) | - | - | - | - | - |
| | Esterase lipase (C8) | - | - | - | - | - |
| | Lipase (C14) | - | 1 | - | - | - |
| | Leucine arilamidase | + | + | + | + | + |
| | Valine arilamidase | + | + | + | + | + |
| | Cystine arilamidase | 2 | 2 | 1 | 1 | 1 |
| | Trypsine | - | - | - | - | - |
| | α-quimiotrypsine | - | - | - | - | - |
| | Acid phosphatase | 1 | | 1 | 1 | 1 |
| | Naftol-AS-BI-phosphohydrolase | + | + | | + | + |
| | α-galactosidase | - | 1 | - | - | 1 |
| | β-galactosidase | + | + | | | + |
| | β-glucuronidase | 1 | 1 | - | - | - |
| | α-glucosidase | + | + | | | + |
| | β-glucosidase | - | - | - | - | - |
| | N-acethyl-β-glucosaminidases | - | - | - | - | - |
| | α-mannosidase | - | - | - | - | - |
| | α-fucosidase | - | - | - | - | - |

TABLE V-continued

Comparison of APIZYM profiles of the selected bacteria using the method described in this invention with other bacteria of the same species.

| | Enzime | LMG 11413 | LMG 13047 | LMG 13134 | LMG 18176 | LMG 18194 | CECT 4479 | CECT 5714 | CECT 5715 |
|---|---|---|---|---|---|---|---|---|---|
| | control | - | - | - | - | - | - | - | - |
| | alcalin phophatase | - | - | - | - | - | - | - | - |
| | Esterase (C4) | 2 | 1 | 1 | 1 | 1 | 1 | 1 | 1 |
| | Esterase lipase (C8) | - | - | - | - | - | - | - | - |
| | Lipase (C14) | - | - | - | - | - | - | - | - |
| | Leucine arilamidase | + | + | + | + | + | + | + | + |
| | Valine arilamidase | 1 | 1 | | | | - | - | 1 |
| | Cystine arilamidase | 1 | 1 | | | | | 1 | 1 |
| | Trypsine | - | - | - | - | - | - | - | - |
| | α-quimiotrypsine | - | 1 | - | - | - | - | - | - |
| | Acid phosphatase | 1 | 2 | | - | 1 | 2 | 1 | 1 |
| | Naftol-AS-BI-phosphohydrolase | | + | + | + | | + | + | + |
| | α-galactosidase | + | - | - | + | - | + | + | + |
| *L. gasseri* | β-galactosidase | | 1 | | - | - | - | - | - |
| | β-glucuronidase | | | - | - | - | - | - | - |
| | α-glucosidase | 1 | | - | 1 | | 1 | - | 1 |
| | β-glucosidase | + | | | + | | | 4 | + |
| | N-acetyl-β-glusosminidases | | 1 | - | | - | - | - | 1 |
| | α-mannosidase | - | - | - | - | - | - | - | - |
| | α-frucosidase | - | - | - | - | - | - | - | - |

| | Enzime | CECT 285 | CECT 4007 | LMG 8900 | LMG 17551 | CECT 5716 |
|---|---|---|---|---|---|---|
| | control | - | - | - | - | - |
| | alcalin phophatase | | - | - | - | - |
| | Esterase (C4) | 3 | | 3 | | 2 |
| | Esterase lipase (C8) | 3 | | 3 | | 3 |
| | Lipase (C14) | - | - | - | - | - |
| | Leucine arilamidase | + | + | + | + | + |
| | Valine arilamidase | 1 | | | 2 | 1 |
| *L. fermentum* | Cystine arilamidase | 1 | | | 1 | 1 |
| | Trypsine | - | - | - | - | - |
| | α-quimiotrypsine | - | - | - | - | - |
| | Acid phosphatase | | | | | 1 |
| | Naftol-AS-BI-phosphohydrolase | | | 3 | 3 | 2 |
| | α-galactosidase | + | | + | | 4 |
| | β-galactosidase | + | + | + | + | + |
| | β-glucuronidase | 1 | - | - | - | - |
| | α-glucosidase | | 4 | | | 3 |
| | β-glucosidase | - | - | - | - | - |
| | N-acetyl-β-glucosaminidases | - | - | - | - | - |
| | α-mannosidase | - | - | - | - | - |
| | α-frucosidase | - | - | - | - | - |

Probiotic strains used were described in Table III. The activities that differ to that observed with the strains of this invention has been indicated in grey.

TABLE VI

Comparison of antibiotic resistances of the selected bacteria using the method described in this invention with other bacteria of the same species.

*L. salivarius*

| Antibiotic | 20492 | 4063 | 4062 | CETC 573 |
|---|---|---|---|---|
| P10 | S | S | S | S |
| E15 | S | S | S | S |
| KF30 | S | S | S | S |
| FOX30 | S | S | S | S |
| CIP5 | R | R | R | S |
| DA2 | S | S | S | S |
| AML25 | S | S | S | S |
| C30 | S | S | S | S |
| CN10 | R | R | R | R |
| TE30 | S | S | S | S |
| CLR15 | S | S | S | S |
| SXT25 | R | R | R | R |
| AMP10 | S | S | S | S |
| NA30 | R | R | R | R |
| VA30 | R | R | R | S |
| MTZ25 | R | R | S | R |

*L. coryniformis*

| Antibiotic | 20005 | 20007 | 4129 | 982 | CETC 5711 |
|---|---|---|---|---|---|
| P10 | S | S | S | S | S |
| E15 | S | S | S | S | S |
| KF30 | S | R | S | S | S |
| FOX30 | S | R | S | R | R |
| CIP5 | R | R | R | R | R |
| DA2 | S | S | S | S | S |
| AML25 | S | S | S | S | S |
| C30 | S | S | S | S | S |
| CN10 | R | R | R | R | R |
| TE30 | S | S | S | S | S |
| CLR15 | S | S | S | S | S |
| SXT25 | I | R | R | R | I |
| AMP10 | S | S | S | S | S |

*L. gasseri*

| Antibiotic | 11413 | 13047 | 13134 | 18176 | 18194 | 4179 | CECT 5714 | CECT 5715 |
|---|---|---|---|---|---|---|---|---|
| P10 | S | S | S | S | S | S | S | S |
| E15 | S | S | S | S | S | S | S | S |
| KF30 | S | S | S | S | S | S | S | S |
| FOX30 | S | S | R | S | S | S | S | S |
| CIP5 | R | R | R | R | R | R | R | R |
| DA2 | S | R | S | R | R | R | S | S |
| AML25 | S | S | S | S | S | S | S | S |
| C30 | S | S | S | S | S | S | S | S |
| CN10 | R | R | R | R | R | R | R | R |
| TE30 | S | S | S | S | S | S | S | S |
| CLR15 | S | S | S | S | S | S | S | S |
| SXT25 | R | R | R | R | R | R | R | R |
| AMP10 | S | S | S | S | S | S | S | S |
| NA30 | R | R | R | R | R | R | R | R |
| VA30 | R | R | R | R | R | I | I | I |
| MTZ5 | R | R | R | R | R | R | R | R |

TABLE VI-continued

Comparison of antibiotic resistances of the selected bacteria using the method described in this invention with other bacteria of the same species.

*L. fermentium*

| Antibiotic | 285 | 4007 | 8900 | 17551 | CETC 5716 |
|---|---|---|---|---|---|
| P10 | S | S | S | S | S |
| E15 | S | S | S | S | S |
| KF30 | S | S | S | S | S |
| FOX30 | R | R | R | R | I |
| CIP5 | R | R | R | R | R |
| DA2 | S | S | S | S | S |
| AML25 | S | S | S | S | S |
| C30 | S | S | S | S | S |
| CN10 | R | R | R | R | R |
| TE30 | S | S | S | S | S |
| CLR15 | S | S | S | S | S |
| SXT25 | R | R | R | R | R |
| AMP10 | S | S | S | S | S |
| NA30 | R | R | R | R | R |
| VA30 | R | R | R | R | R |
| MTZ5 | R | R | R | R | R |

Probiotic strains used were described in Table III. The antibiotics used and the methodology is described in example 4e. R=resistant, I=intermediate, S=sensible. The activities that differ to that observed with the strains of this invention has been indicated in grey.

Example 4

Probiotic Characteristics of the Strains

We also analyzed the suitability of the probiotic selection process included in this invention regarding its ability to select bacterial strains with desirable probiotic characteristics. In order to evaluate this, the selected strains were analyzed for a high number of different characteristics that could enhance their capabilities to act as a probiotic strains. Moreover, we assigned arbitrarialy (as indicated) a numerical value to the results obtained in each test in order to compare the probiotic strain included in this invention to those obtained by other selection criteria. The results obtained are summarized in Table VIII at the end of this example and described in the following sub-examples and compared with some commercial strains.

Example 4a

Adhesion Analysis to Caco-2 and HT-29

Culture of Caco-2 and HT-29 Cells

For the adhesion and inhibition assays, the cell lines Caco-2 (ATCC HTB-37) and HT-29 (ATCC HTB-38) were utilized as a model of the intestine cells. Both cell lines presented features characteristic for intestinal cells such as polarization, expression of intestinal enzymes, and production of particular structural polypeptides and mucins.

The cells were grown in plastic flasks (75 cm$^2$, Nunc) in DMEM (PAA laboratories) as culture medium supplemented with 10% inactivated FCS (Fetal Calf Serum, PAA laboratories), non essential aminoacids, 100 U/ml penicilline/streptomycine, 1 µg/ml amphoterine. Cell culture was performed at 37° C. in an atmosphere comprising 95% air and 5% $CO_2$. Media was changed on a two daily basis and the cells were splitted every week.

For the adhesion assays the cells were splitted to 35 mm plastic dishes (Nunc) and cultured in similar conditions but without antibiotics after confluence. Adhesion assays were performed 10-14 days post-confluence.

Culture of Bacteria

Probiotic strains:

The probiotic strains of this invention were cultured in MRS broth (pH 6.2) in anaerobic conditions for 16-18 hours at 37° C. after inoculation of a 0.1% (v/v) from the glycerol stock. In this conditions, the concentration of the culture was $1-2\times10^9$ cfu/ml, as observed by plating on MRS agar.

Gram-negative strains: *Escherichia coli* O157:H7 (non-pathogenic) (CECT4972), *E.coli* O157:H7 (enteropathogenic) (CECT4783), *E.coli* O157:H7 (enteropathogenic) (CECT4782), *Salmonella cholerasuis typhi* (CECT409) and *S. cholerasuis typhimurium* (CECT443) were all obtained from the CECT-Colección Española de Cultivos Tipo—. All gram negatives strains were cultured in TSB broth (AES Laboratoire) in anaerobic conditions for 16-18 hours at 37° C. after inoculation of a 0.1% (v/v) from the glycerol stock. At this conditions, the concentration of the culture was $1-2\times10^9$ cfu/ml, as observed by plating on TSA agar (AES Laboratoire).

Adhesion Analysis

Caco-2 and HT-29 intestinal cell lines were cultured in 35 mm plastic dishes in 2 ml medium without antibiotics to confluence. 10-14 days post-confluence 1 ml of media was replaced with 1 ml of a suspension of 108 bacteria in DMEM. The cultures were incubated 1 hour at 37° C. After that, cells were washed twice with PBS and fixed with ice-cold 70% methanol for 30 minutes. Plates were air dried and Gram stained. The attached bacteria were visualized using an optical Axiovert 200 (Zeiss) microscope at 1000× magnification in oil-immersion. Twenty randomized fields were counted and the results expressed as the mean of the number of bacteria attached to the cells per field±SD. The capability of a probiotic strain was considered high if the number of attached bacteria was >250, moderate between 100 and 250, and
slight >100 (FIG. 5)

Example 4b

Resistance to Acid and Bile Salts

To analyze the resistance of the probiotic strains of this invention to acidic and high bile salt content, conditions that these bacteria will encounter during the digestive transit, bacteria were cultured in MRS broth media either at pH 3.0 or in MRS broth at pH 6.2 supplemented with 0.15% bile salts (Sigma) for 90 minutes. The survival rate was calculated by MRS agar plating of serial dilutions and compared to the number of colonies obtained in control conditions (MRS broth pH 6.2). Plates were cultured 16-18 hours at 37° C. in anaerobic conditions. The experiment was repeated three times. Resistance was considered high when the survival was >80%, moderate 80% to 60%, slight <60% compared with the control conditions (FIG. 6).

Example 4c

Time of Generation

The time of generation, meaning the time that a bacterial culture requires to duplicate the concentration of bacteria, is an important characteristic for a probiotic bacteria. It is important from an industrial point of view (production of a higher amount of biomass in the same amount of time) and from a probiotic point of view (higher colonization of the gut). In order to consider both aspects we have analyzed the generation time of the probiotic strains of the invention in a rich media (industrial point of view) and in a poor media (probiotic point of view).

The probiotic strains of this invention were grown in MRS broth (pH 6.2) with 2% (rich media) or 0.2% (poor media) glucose for 0, 1, 2, 4 and 6 hours at 37° C. in anaerobic conditions and the concentration of bacteria was determined by plating serial dilutions in MRS agar plates and incubation of the plates for 16-18 hours at 37° C. in anaerobic conditions (FIG. 7). The generation time was calculated as the time in minutes necessary in order to duplicate the number of colonies at the initial time.

Example 4d

Fermentation Capabilities

The capacity of a bacterial strain to metabolize complex carbohydrates (soluble and non-soluble fibers) ensures that these probiotic strains could use them as a carbon source in the colon, and thus enhance the efficiency of colonization. For this reason, we have tested the capability of the probiotic strains of this invention to use several non-digestible fibers as an unique source of carbohydrates.

To assay the capability to the probiotic bacterial strains to metabolize fiber we cultured, a liquid culture was carried out in MRS broth media without glucose and supplemented with a 2% of each fiber in 96 well flat-bottomed plastic dishes (Nunc) for 24 and 48 hours at 37° C. in anaerobic conditions. The fermentation process was controlled by pH decrease in the media and determined by a calorimetric approach using 0.3% phenol red as indicator and measuring the absorbance at 540 nm.

The fibers used were: ☐-celulose (raw cellulose, Campi y Jove), Actilight (fructo-oligosaccharide, Beghin-Meiji), Ficao (cocoa fiber, Natra), Fructafit (Inulin, Sensus), Lactose (Bordulo), Pectine (YM100, Genu), Raftiline (Inulin oligofructose, Orafti), Raftilose (Inulin oligofructose, Orafti), and Vitacel (purified cellulose, Campi y Jove).

The fermentation capability (defined as fold-induction of the pH reduction compared to the control without fiber) was calculated. Results showed in FIG. 8 represent the individual values for each fiber (panel A) and the sum of all these individual values for each selected strain (Panel B). Fermentation capability was considered high when the sum of individual values was >30, moderate 30 to 25, slight <25.

Example 4e

Resistance to Antibiotics

The use of antibiotics leads to a reduction of the comensal gut microflora which sometimes relates to diarrhea and other gut disorders. Moreover, this reduction in the amount of gut bacteria could be the consequence of opportunistic pathogenic bacteria and viruses to infect the host. The use of antibiotics to block the infection does not resolve this disorder but complicates it. In other situations like intestinal inflammation where probiotics could exert a beneficial role, this potential effect is sometimes limited by the simultaneous therapy with antibiotics. For these reasons, the selection of potential probiotic strains able to resist common antibiotics would be an improvement in the art.

To analyze the resistance of the probiotic strains of this invention an agar well diffusion assay was used. Mueller-Hinton agar plates containing $10^6$ cfu/ml of each probiotic strain were prepared. Then, antibiotic commercial discs corresponding to the indicated concentrations were added to the wells and allowed to diffuse into the agar during a preincubation period of 10 minutes at room temperature, followed by anaerobic incubation of the plates at 37° C. for 16-18 hours. Diameter of inhibition halos was measured and the resistance degree of the bacteria to each antibiotic was graded as R (resistant), I (intermediate) or S (sensible) according to the described sensibility of lactobacilli to this antibiotics (Table VII). After that, a numerical value was assigned to each condition: R=3, I=2, and S=1. Ten different antibiotics were tested and the numerical values were added up to get an overall value. The resistance capability of a probiotic strain was considered high if the total value was >17, moderate between 15 and 17, and slight <15.

The antibiotics and concentrations used were: Erythromycin 15 mg (E 15), Penicillin 10 µg (P 10), Ciprofloxacin 5 µg (CiP 5), Chloramphenicol 30 µg (C 30), Nalidixic 30 µg Na 30), Amoxicilin 10 µlg (AM 10), Tetracycline 30 µg (Te 10), Vancomicin 30 µg (Va 30), Cephoxithin 30 µg (Fox 30), and Cephalothin 30 µg (CF 30) (FIG. 9).

inoculated with $10^8$ cfu of each bacterial strain and fermented for 24 (grey bars) and 48 (black bars) hours at 37° C. in anaerobic conditions and the pH was measured using a CyberScan 510 pHmeter (VWR). The production of acid by a probiotic strain was considered high if the milk pH value after 48 hours was <4.5, moderate between 4.5 and 5.5, and slight >5.5 (FIG. 10).

Example 4g

Production of Antimicrobial Metabolites

It has been suggested that the main beneficial effect of probiotics is the control of the balance between useful and harmful intestinal bacteria is the gut. When the number of useful bacteria is reduced, opportunistic bacteria could overgrow and disturb the well-being of the host or even induce an infection. Most bacterial organisms have adquired characteristics or mechanisms that reduce the growth capabilities of other microorganisms that cohabitate with them and thus, enabling their selective growth. As stated in example 4f, the reduction of pH through acid production by lactic acid bacteria is one of such mechanisms. Moreover, some lactic bacteria also produce bioactive peptides components and other metabolites that selective inhibit the growth of other bacteria, yeast or fungi. This is the case of bacteriocins such as pediocin.

The probiotic strains of this invention were assessed for their capability to produce antimicrobial metabolites using an agar well diffusion assay. MRS agar plates containing $10^6$ cfu/ml of different pathogenic bacteria strain (*Salmonella*

TABLE VII

Resistance of the selected strains to antibiotics.

| TEST | CECT5711 | CECT5713 | CECT5714 | CECT5715 | CECT5716 | LGG | LA1 | LC |
|---|---|---|---|---|---|---|---|---|
| E15 | S | S | S | S | S | S | R | R |
| P10 | S | S | S | S | S | S | S | S |
| CIP5 | R | I | R | R | R | I | R | R |
| C30 | S | S | S | S | S | S | S | S |
| Na30 | R | R | R | R | R | R | R | R |
| Am10 | S | S | S | S | S | S | S | S |
| Te30 | I | S | S | S | S | S | S | S |
| Va30 | R | R | I | I | R | R | S | S |
| Fox30 | R | S | R | R | R | R | R | R |
| CF30 | S | S | I | I | S | I | I | I |
| Total | 19 | 15 | 16 | 18 | 19 | 17 | 18 | 18 |

Example 4f

Production of Metabolic Acids

The production of metabolic acids by probiotic bacteria, namely lactic, acetic, propionic and butyric acid, and the subsequent reduction of the pH in feces has been extensively associated with a beneficial effect of these bacteria due to a reduction in the growth and infective capabilities of opportunistic pathogenic microorganisms. Moreover, some of these acids, specially butyric acid, are rapidly absorbed and used by the intestinal cells as an energy source. In this sense, reduced pH in feces of the breast feeding infants has been associated with the reduced risk of gut disorders compared with formula feeding babies.

Acid producing capacity of the probiotic strains of the invention was observed by measurement of the pH reduction during milk fermentation. Five ml of skimmed milk were

*typhmurium* and *Escherichia coli*) were prepared. Wells, with a diameter of 5 mm, where then cut in the agar using a sterile cork-borer. Then, 50 µl of a 2 fold concentrate supernatant of each probiotic strain culture were added to the wells and allowed to diffuse into the agar during a 2 hours preincubation period at 4° C., followed by aerobic incubation of the plates at 37° C. for 16-18 hours. The antimicrobial activity of each supernatant was considered high if the diameter of the inhibition hallo for both pathogenic bacteria strains was >12, moderate between 8 and 12, and slight <8 (FIG. 11)

Moreover, it was also tested if the antimicrobial activity of the supernatants was due to a antimicrobial substance or to the production of metabolic acids. In this sense, the inhibitory effect of a dilution of each metabolic acid (acetic, lactic, propionic and butyric) at pH 4.5 was assayed. None of these situations inhibited the growth of *Salmonella* or *E. coli* in these conditions (data not shown). It was also tested the antimicrobial capabilities of supernatants obtained from bacterial cultures using glucose or lactose as a carbohydrate source. In these circumstances, those bacterial strains that do not ferment lactose (*L. rhamnosus* GG and *L. acidophilus* CECT5714) did not showed antimicrobial activity in the lactose-containing culture whereas they showed this activity it in the glucose culture (data not shown).

Example 4h

Inhibition of Pathogen Adhesion to Caco-2

Caco-2 intestinal cell lines were cultured in 35 mm plastic dishes in 2 ml complete medium without antibiotics to confluence. 10-14 days post-confluence 1 ml of media was replaced with 1 ml of a suspension of $10^8$ probiotic bacteria in DMEM. The cultures were incubated 1 hour at 37° C. After that, 1 ml of a suspension of 108 pathogenic bacteria (*E. coli* or *S. typhimurium*) in DMEM was added to the cultures and incubated 1 hour more at 37° C. The cells were washed twice with PBS and fixed with ice-cold 70% methanol for 30 minutes. Plates were air dried and Gram stained. The attached bacteria were visualized using an optical Axiovert 200 (Zeiss) microscope at 1000× magnification in oil-immersion. The number of gram-negative bacteria in 10 randomized fields were counted and the results expressed as the mean of % of pathogenic bacteria attached to the cells compared to control cultures without probiotic strains. The capability to inhibit the adhesion of pathogenic bacteria to intestinal cells of a probiotic strain was considered high if the % of both strains of Gram-negative attached bacteria as compared with the control was <25%, moderate between 25% and 75%, and slight >75% (FIG. 12).

All the results obtained in the example 4 are summarized in Table VIII. Each test was performed as indicated in the corresponding sub-example and described in this document. The categories in each test were assigned as indicated. a) Example 4a; number of bacteria attached per field; high >250, moderate: 100 to 250, slight <100. b) Example 4b; % of survival compared to control conditions; high >80%, moderate: 80% to 60%, slight <60%. c) Example 4c; minutes necessary to duplicate de initial population; rapid <60, moderate: 60 to 120, slow >120. d) Example 2; number of fermentable substrates; high >18, moderate, 12 to 18, slight <12. e) Example 4d; Accumulated fold-reduction of the total fermentable substrates compared with the control; high >30, moderate: 25 to 30, slight <25. f) Example 4e, Accumulated resistance to each antibiotic (resistant =3, intermediate =2, sensible =1); high >17, moderate: 15 to 17, slight <15. g) Example 4f; p value of milk after 48 hours culture; high <4, moderate: 4 to 4.5, slight >4.5. h) Example 4g; mm of inhibition hallo high >12, moderate: 12 to 8, slight <8, (*) only in presence of glucose but not lactose. i) Example 4h; % of adhesion; high <25, moderate: 25 to 75, slight <75. The global probiotic capability was calculated by the sum of all tests (high=3, moderate=2, slight=1).

TABLE VII

Potency to act as a probiotic of the different strains of the invention. The different capabilities to act as a probiotic of the different strains of the invention were compared to those observed in some commercial probiotic strains (*Lactobacillus rhamnosus* LGG from Valio, *Lactobacillus johnsonii* La1 from Nestlé and *Lactobacillus casei immunitas* from Danone) and quantificated arbitrarially.

| TEST | CECT5711 | CECT5713 | CECT5714 | CECT5715 | CECT5716 | LGG | LA1 | LC |
|---|---|---|---|---|---|---|---|---|
| Adhesion to Caco-2[a] | high | moderate | high | high | high | high | high | slight |
| Adhesion to HT-29[a] | high | high | moderate | moderate | high | high | moderate | slight |
| Resistance to acid[b] | high | moderate | high | moderate | high | moderate | slight | slight |
| Resistance to bile[b] | high | high | slight | slight | moderate | slight | high | high |
| Time of generation[c] | moderate | rapid | moderate | slow | moderate | rapid | moderate | moderate |
| APICH50[d] | slight | high | moderate | high | moderate | moderate | moderate | high |
| Fermentation[d] | moderate | high | slight | slight | slight | slight | high | high |
| Antibiogam[f] | high | slight | moderate | high | high | moderate | high | high |
| Reduction of pH[g] | high | moderate | moderate | moderate | moderate | slight | moderate | slight |
| Antimicrobial prod.[h] | high | high | high(†) | moderate | moderate | moderate(†) | slight | slight |
| Pathogen Inhibition[i] | high | high | moderate | high | high | high | moderate | slight |
| Probiotic capability | 29 | 28 | 23 | 23 | 26 | 23 | 24 | 20 |

Example 5

Probiotic Colonization of Mice Gut

By definition, a probiotic must colonize the gut mucosa of the host. Moreover, it has been described that the beneficial actions exerted by probiotics require this colonization. Although in vitro studies such as adhesion capabilities to intestinal cell lines, or resistance to the digestion conditions are good approaches to select probiotic strains, these tests do not ensure the effectiveness of the selected strain to colonize in vivo the gut mucosa. For this reason, we performed an analysis in vivo of the colonization capacity of the probiotic strains of the invention using mouse as an experimental animal model.

Six male Balb/c mice (6-8 weeks old) were daily supplemented with $10^8$ cfu in 0.2 ml of skimmed milk of *L. salivarius* CECT5713 for 14 days. After this period, the probiotic supplementation was stopped but the animals were still kept in observation for another 14 days. Feces samples were collected at 0, 7, 14, 21 and 28 days from the initiation of the experience. Aprox. 200 mg of feces were collected independently from each mice and homogenized at 50 mg/ml in peptone water. Serial dilutions of the collected supernatant were prepared, and 0,1 ml plated in selective agar plates (MRS for *Lactobacilli*, Eugon agar+tomato juice for Bifidobacteria and McConkey agar for coliform bacteria). Plates were incubated at 37° C. in anaerobic conditions for 24 hours. The number of cfu was determined by counting on selective media plates and the verage was calculated.

FIG. 13 shows that supplementation with *L. salivarius* CECT5713 caused a stadistically significant increase in the number of total lactobacilli in feces which demonstrates that this strain is able to survive its passage through the digestive tract and reach the colon. Moreover, the fact that the increased lactobacilli count was still observable one week after finalization of the oral supplementation demonstrates that this probiotic strain is able to temporally colonize the gut mucosa.

Concomitantly with the *lactobacilli* increase, a reduction in the fecal count of coliform bacteria was also observed, and was still statistically significant two weeks after finalization of the probiotic treatment. These findings show that dietary supplementation with CECT5713 cells causes not only stimulation of the beneficial flora but also inhibition of the harmful bacteria.

Example 6

Effect of *Lactobacillus fermentum* CECT5716 on Translocation of *Salmonella typhimurium* in Mice Following Immunization with Inactivated *Salmonella* Vaccine Translocation of Gram-negative bacteria across the gut epithelium can occur especially in subjects following gastrointestinal infection, disease or surgery. Left untreated it can lead to endotoxemia. In this example, the effect of feeding *L. fermentum* CECT5716 on the translocation of gut pathogen *Salmonella typhimurium* was examined.

Male Balb/c mice (6-8 weeks old) were daily orally inoculated with $1\times10^8$ cfu in 0.2 ml of milk or milk alone for two weeks. After that, mice were immunized orally or not with an inactivated *Salmonella* vaccine ($10^8$ cfu inactivated with paraphormaldehyde in 0.2 ml milk). After immunization, mice were orally inoculated two weeks more with the *L. fermentum* CECT5716 preparation in alternate days for two weeks more. Two weeks after oral immunization, all mice were orally challenged with live *S. typhimurium* ($10^{10}$ cfu in 0.2 ml milk). Then, after 24-48 hours, the level of colonization of *S. typhimurium* in the spleen was determined by colony counting in SS agar (Oxoid). The fecal concentration of IgA specific for *Salmonella* antigens were also measured by ELISA techniques (Biosource).

The results obtained demonstrate that *L. fermentum* CECT5716 potentiates the beneficial effect of the vaccination of mice with the inactivated *Salmonella* vaccine as shown in FIG. 15. The inhibition on the translocation of *S. typhimurium* induced by the inactivated vaccine and potentiated by *L. fermentum* CECT5716 was due to the increase of the secretion of specific IgA and also, to the inhibition or blocking effect of the probiotic strain on the mucosal adhesion of *Salmonella* as described in Example 4h.

Example 7

Effect of Probiotic Bacteria on Inflammatory Cytokines

Besides the reduction of the risk of infection, many clinical effects associated to probiotic treatments are due to immunomodulatory capabilities of selected probiotic strains. The regulation of the immune response is usually mediated through a change in the balance between pro-inflammatory cytokines (Th1) such as TNF-α, humoral cytokines (Th2) such as IL-4 or IL-13, and regulatory cytokines (Th3) such as IL-10 and TGF-β. For this reason, the effect of some of the probiotic strains of this invention in regulating the expression of some of these crucial cytokines was also tested.

Bone marrow derived macrophages were stimulated with 100 ng/ml of LPS (Sigma) as a cellular model. $10^5$ macrophages/well were cultured in 24-well plastic plates (Nunc) with 1 ml of DMEM. Once attached, macrophages were stimulated or not with 100 ng/ml LPS and with $10^7$ cfu/ml of the indicated probiotic strains for 12 hours at 370C. in a 5% $CO_2$ atmosphere. Supernatants were collected and the production of cytokines was analyzed using a mouse TNF-α or mouse IL-10 ELISA (Biosource). The results obtained (FIG. 15) show that the consumption of the probiotic strains of this invention could have a beneficial effect in some inflammatory situations since they induce a global anti-inflammatory effect on immune cells such as macrophages, inducing an increase in IL-10 expression without increasing the levels of secreted TNF-α.

Example 8

Effect of Probiotic Bacteria on Ig Production

The effect of the probiotic strains of this invention on the immunoglobulin production was analyzed using lymphocyte cultures obtained from the spleen of male Balb/c mice (6-8 weeks old). $2\times10^6$ lymphocytes were cultured in 1 ml DMEM in 24 well plastic plates and stimulated with inactivated probiotic cultures ($10^8$ cfu/ml) in presence or absence of 25 µg/ml LPS for 6 days. The production of Ig G by lymphocytes was assessed using a mouse Ig G ELISA from Bethyl.

The results obtained (FIG. 16) show that the effect on the Ig G production induced in lymphocytes of the probiotic strains of this invention is highly variable depending on the selected strain used. In this regard, there is some strains (CECT5711 and CECT5714) that have immune-stimulating activities since induce the expression of Ig G, while others (CECT5713 and CECT5715) have immune-suppressive effects.

Example 9

Preparation of a Fermented Liquid Milk Formula

A normal fermented liquid milk composition with probiotics was prepared using the following formula:

| | |
|---|---|
| Milk 1.5% Fat; 3.2% protein | 997 g/kg |
| Skim milk powder | 3 g/kg |
| Probiotic strain ($10^{12}$ cfu/g) | 0.1 g/kg |

The fat and dry solids contents of the milk were standardized according to the formulation described above. After that, the milk was homogenized at 20-25 Mpa and 65-70° C. to obtain optimum physical properties in the product. The preparation was heated at 90-95° C. and a holding time of about 5 minutes. This period of time causes the denaturation of about 70-80% of whey proteins. Cooled milk (40-45° C.) was inoculated with the probiotic strain in absence of any starter culture and fermented in the incubation tank at 40-45° C. for 10 hours without agitation until reaching a final pH (pH 4.5-5). After clot formation, is the mixture was homogenized by mechanical methods. Once the homogenization was carried out, the preparation was cooled down to a temperature below 10° C. in 60 minutes. After that, the composition was packaged. Final cooling, normally down to 5° C., took place in a cold room, where the products were held to caducity.

Example 10

Preparation of a Set Yogurts

A yogurt product with probiotics was prepared using the following formula:

| Milk 3.1% Fat; 3.2% protein | 987 g/kg |
| Skim milk powder | 13 g/kg |
| Starter | 0.1 g/kg |
| Probiotic strain ($10^{12}$ cfu/g) | 0.1 g/kg |

The fat and dry solids contents of the milk were standardized according to the formulation described above. The milk was homogenized at 20-25 Mpa and 65-70° C. to obtain optimum physical properties in the product and heat treatment was performed at 90-95° C. and a holding time of about 5 minutes which is able to denature about 70-80% of whey proteins. After pasteurization, milk was cooled to 40-45° C. and the starter and probiotic cultures were metered into the stream of milk as they were pumped from an intermediate storage tank to the filling machine. Following packaging in the filling machine, the packages after crating and palletizing, were trucked into the system for incubation and cooling. After that, filled pallets were fermented in the incubation room at 40-45° C. for 5-6 hours until a pH of 4.5 was reached. Cooling of the packets were performed quickly obtaining a temperature of 12-15° C. in 55-70 minutes. Final cooling, down to 5° C., took place in the chill store.

Example 11

Preparation of an Infant Formula in Powder

An infant formula with probiotics was prepared using the following formula:

| Demineralised whey | 512 g/kg |
| Palm olein | 135 g/kg |
| Lactose | 92 g/kg |
| Skimmed Milk | 95 g/kg |
| Rapeseed oil | 52 g/kg |
| Coconut oil | 49 g/kg |
| Sunflower oil | 28 g/kg |
| Water | 31 g/kg |
| Vitamin premix | 2 g/kg |
| Mineral premix | 4 g/kg |
| Probiotic strain ($10^{12}$ cfu/g) | 0.1 g/kg |

To an appropriately sized blend tank with agitation and heating all solid ingredients were mixed with the liquid milk and water in the absence of any vitamins. Then, the vegetable oils were admixed. The mixture was then heated at 60-70° C. and emulsified through a single stage homogenizer at 6 to 7 MPa in absence of oxygen. After emulsification the mixture was standardized by addition of vitamins and the pH was adjusted in the range of about 6.7 to 7.2. Then, the mixture was reheated to between about 65° C. and 70° C. The product was finally was dried in a spray drier to obtain a final dry powder product. Finally, the probiotic strain ($10^{12}$ cfu/g) (0.1 g/Kg) was dry mixed with the final dry powder product and was packaged.

---

The invention claimed is:

1. A biologically pure culture of *Lactobacillus coryniformis* strain CECT-5711.

2. A biologically pure culture of *Lactobacillus salvarius* subspecies *Salivarius* strain CECT-5713.

3. A biologically pure culture of *Lactobacillus gasseri* strain CECT-5714.

4. A biologically pure culture of *Lactobacillus gasseri* strain CECT-5715.

5. A biologically pure culture of *Lactobacillus fermentum* strain CECT-5716.

* * * * *